United States Patent
Ito et al.

(10) Patent No.: US 9,029,113 B2
(45) Date of Patent: May 12, 2015

(54) MODIFIED AMINOTRANSFERASE, GENE THEREOF, AND METHOD FOR PRODUCING OPTICALLY ACTIVE AMINO COMPOUND USING SAME

(75) Inventors: Noriyuki Ito, Takasago (JP); Shigeru Kawano, Takasago (JP); Yoshihiko Yasohara, Takasago (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 14/004,293

(22) PCT Filed: Mar. 9, 2012

(86) PCT No.: PCT/JP2012/056174
§ 371 (c)(1),
(2), (4) Date: Sep. 10, 2013

(87) PCT Pub. No.: WO2012/124639
PCT Pub. Date: Sep. 20, 2012

(65) Prior Publication Data
US 2014/0004575 A1 Jan. 2, 2014

(30) Foreign Application Priority Data
Mar. 11, 2011 (JP) ................. 2011-054636

(51) Int. Cl.
*C12N 9/10* (2006.01)
*C12P 17/12* (2006.01)
*C12P 13/00* (2006.01)
*C12P 13/04* (2006.01)
*C12P 41/00* (2006.01)

(52) U.S. Cl.
CPC ............ *C12N 9/1096* (2013.01); *C12P 13/001* (2013.01); *C12P 13/04* (2013.01); *C12P 41/006* (2013.01)

(58) Field of Classification Search
None
See application file for complete search history.

(56) References Cited

U.S. PATENT DOCUMENTS

| | | |
|---|---|---|
| 2009/0148899 A1 | 6/2009 | Kawano et al. |
| 2010/0285544 A1 | 11/2010 | Ito et al. |

FOREIGN PATENT DOCUMENTS

| | | |
|---|---|---|
| WO | WO-2006/126498 A1 | 11/2006 |
| WO | WO-2007/139055 A1 | 12/2007 |

OTHER PUBLICATIONS

Noriyuki Ito et al., "*Pseudomonas fluorescens* Yurai no Shinki Amino Ki Ten'i Koso Idenshi no Cloning to Gai Koso o Mochiita Kogaku Kassei Amine Rui no Gosei", Japan Society for Bioscience, Biotechnology, and Agrochemistry 2009 Nendo (Heisi 21 Nendo) Taikai Koen Yoshishu, Mar. 5, 2009, p. 122 2P0974B.
Noriyuki Ito et al., "Amino Ki Ten'i Koso o Mochiita Kogaku Kassei Amine Rui no Koritsuteki na Gosei", Japan Society for Bioscience, Biotechnology, and Agrochemistry 2010 Nendo (Heisei 22 Nendo) Taikai Koen Yoshishu, Mar. 5, 2010, p. 93 2AUa09.
International Search Report issued in Application No. PCT/JP2012/056174 dated Apr. 3, 2012.

*Primary Examiner* — Suzanne M Noakes
(74) *Attorney, Agent, or Firm* — Novak Druce Connolly Bove + Quigg LLP

(57) ABSTRACT

Provided is a method for efficiently producing from a ketone compound an optically active amino compound useful as an intermediate of a drug, an agricultural chemical, or the like. Provided are: a polypeptide having aminotransferase activity that is increased in stereoselectivity, heat resistance, and resistance to amine compounds compared to the wild type enzyme by means of modifying an aminotransferase derived from *Pseudomonas fluorescens*; a gene encoding the polypeptide; and a transformant that expresses the gene at a high level.

20 Claims, No Drawings

SEQUENCE LISTING

```
<160> NUMBER OF SEQ ID NOS: 42

<210> SEQ ID NO 1
<211> LENGTH: 454
<212> TYPE: PRT
<213> ORGANISM: Pseudomonas fluorescens
```

<400> SEQUENCE: 1

```
Met Asn Ser Asn Asn Lys Ala Trp Leu Lys Glu His Asn Thr Val His
1               5                   10                  15
Met Met His Pro Met Gln Asp Pro Lys Ala Leu His Glu Gln Arg Pro
            20                  25                  30
Leu Ile Ile Gln Ser Gly Lys Gly Val His Ile Thr Asp Val Asp Gly
        35                  40                  45
Arg Arg Phe Ile Asp Cys Gln Gly Gly Leu Trp Cys Val Asn Ala Gly
50                  55                  60
Tyr Gly Arg Arg Glu Ile Ile Asp Ala Val Thr Arg Gln Met Glu Glu
65                  70                  75                  80
Leu Ala Tyr Tyr Ser Leu Phe Pro Gly Ser Thr Asn Ala Pro Ala Ile
                85                  90                  95
Ala Leu Ser Gln Lys Leu Thr Glu Val Ala Ala Glu Glu Gly Met Val
            100                 105                 110
Lys Ala Ser Phe Gly Leu Gly Gly Ser Asp Ala Val Glu Thr Ala Leu
        115                 120                 125
Lys Ile Ala Arg Gln Tyr Trp Lys Leu Glu Gly Gln Pro Asp Lys Val
130                 135                 140
Lys Phe Val Ser Leu Tyr Asn Gly Tyr His Gly Leu Asn Phe Gly Gly
145                 150                 155                 160
Met Ser Ala Cys Gly Gly Asn Ala Trp Lys Ser Ser Tyr Glu Pro Leu
                165                 170                 175
Met Pro Gly Phe Phe Gln Val Glu Ser Pro His Leu Tyr Arg Asn Pro
            180                 185                 190
Phe Thr Asn Asp Pro Glu Glu Leu Ala Glu Ile Cys Ala Gln Ile Leu
        195                 200                 205
Glu Arg Gln Ile Glu Met Gln Ala Pro Gly Thr Val Ala Ala Leu Ile
210                 215                 220
Ala Glu Pro Ile Gln Gly Ala Gly Gly Val Ile Val Pro Pro Ala Ser
225                 230                 235                 240
Tyr Trp Pro Arg Leu Arg Gln Ile Cys Asp Lys Tyr Asp Ile Leu Leu
                245                 250                 255
Ile Ala Asp Glu Val Ile Thr Gly Leu Gly Arg Ser Gly Ser Leu Phe
            260                 265                 270
Gly Ser Arg Gly Trp Gly Val Lys Pro Asp Ile Met Cys Leu Ala Lys
        275                 280                 285
Gly Ile Ser Ser Gly Tyr Val Pro Leu Ser Ala Thr Leu Val Asn Ser
290                 295                 300
Arg Val Ala Arg Ala Trp Glu Arg Asp Ala Gly Phe Thr Ser Val Tyr
305                 310                 315                 320
Met His Gly Tyr Thr Tyr Ser Gly His Pro Val Ser Cys Ala Ala Ala
                325                 330                 335
Leu Ala Ala Ile Asp Ile Val Leu Gln Glu Asn Leu Ala Glu Asn Ala
            340                 345                 350
Arg Val Val Gly Asp Tyr Phe Leu Glu Lys Leu Ile Leu Lys Asp
        355                 360                 365
Lys His Arg Ala Ile Gly Asp Val Arg Gly Lys Gly Leu Met Leu Ala
370                 375                 380
Val Glu Leu Val Lys Glu Arg Ala Thr Lys Glu Pro Phe Gly Pro Ala
385                 390                 395                 400
Asp Ala Tyr Pro Leu Ala Ile Ser Glu Ala Cys Val Asn Asn Gly Val
                405                 410                 415
```

```
Met Ile Arg Thr Ile Val Asn Lys Leu Ile Ile Ser Pro Pro Leu Thr
            420                 425                 430

Phe Thr Thr Glu His Val Asp Glu Val Ile Glu Val Leu Asp Arg Ala
        435                 440                 445

Phe Val Ala Asn Pro Trp
    450

<210> SEQ ID NO 2
<211> LENGTH: 1365
<212> TYPE: DNA
<213> ORGANISM: Pseudomonas fluorescens

<400> SEQUENCE: 2
atgaacagca acaacaaagc ctggctcaaa gagcacaaca cggtgcacat gatgcatccg      60
atgcaggatc cgaaagcact gcacgaacag cgcccattga ttattcagtc cggtaagggc     120
gtacacatca ctgatgttga cgggcgtcgc ttcatcgatt gccagggcgg actatggtgc     180
gtcaatgccg gttacggtcg acgtgaaatc atcgacgcgg tgacccggca gatggaagag     240
ctggcgtact attcgttgtt tcccggcagc accaatgcgc cggccattgc gctttcgcag     300
aagttgacca aggtggcggc cgaggagggc atggtcaagg catcgtttgg tctcggcggt     360
tcggacgccg tggagactgc gctgaaaatc gctcgtcaat actggaagct ggaaggccag     420
cccgacaagg tcaagttcgt ctcgttgtac aacggctatc acggcctgaa cttcggtggc     480
atgtccgcct gtggcggcaa cgcctggaaa agcagctacg aacccttgat gccgggcttc     540
ttccaggtcg aatcaccgca tctataccgc aaccctttca ccaatgatcc agaggaactc     600
gcagaaatct gtgcgcagat ccttgagcgg caaatcgaaa tgcaagcgcc gggcactgtc     660
gcggcgttga ttgccgagcc gatccaggga gctggcggag tcatcgtacc ccagcctct     720 tattggccgc gcttgcgcca gatctgcgac aagtatgaca ttctactgat cgccgatgag     780
gtcatcaccg gactgggtcg cagcggttcg ttgttcggtt ccgtggttg ggggtcaag     840 cccgacatca tgtgcctggc aaaaggtatc agcagcggtt atgtgcctct gagcgcgaca     900
ctggtcaact cccgcgtcgc ccgggcatgg gagcgtgatg ccggtttcac ctcggtctac     960
atgcatggct acacctattc cggtcaccct gtctcttgcg ccgctgcgct ggcggccatc    1020
gacatcgtgc tgcaggagaa tctcgccgaa aacgcacggg tggttggcga ctatttcctg    1080
gagaagctgc tgatactcaa ggacaaacat cgggccatcg gcgatgtgcg cggcaagggg    1140
ctgatgctgg cagtcgagct ggtcaaggaa agggcgacca aggagccgtt cggcccggca    1200
gacgcttatc cgctggccat ttccgaggcc tgtgtgaata acggagtgat gattcgtacc    1260
atcgtcaaca gctgatcat ctcgccgccg ttgaccttca ccaccgagca tgtcgacgaa    1320
gtgatcgagg tgctcgaccg cgccttcgtt gccaaccct ggtaa                      1365

<210> SEQ ID NO 3
<211> LENGTH: 32
<212> TYPE: DNA
<213> ORGANISM: Artificial
<220> FEATURE:
<223> OTHER INFORMATION: primer

<400> SEQUENCE: 3
tggagtggcc atatgaacag caacaacaaa gc                                     32

<210> SEQ ID NO 4
<211> LENGTH: 33
```

<212> TYPE: DNA
<213> ORGANISM: Artificial
<220> FEATURE:
<223> OTHER INFORMATION: primer

<400> SEQUENCE: 4
tggtcagcga attcttacca ggggttggca acg                              33

<210> SEQ ID NO 5
<211> LENGTH: 33
<212> TYPE: DNA
<213> ORGANISM: Artificial
<220> FEATURE:
<223> OTHER INFORMATION: primer

<400> SEQUENCE: 5
gaagagctgg cgtactgttc gttgtttccc ggc                              33

<210> SEQ ID NO 6
<211> LENGTH: 33
<212> TYPE: DNA
<213> ORGANISM: Artificial
<220> FEATURE:
<223> OTHER INFORMATION: primer

<400> SEQUENCE: 6
gccgggaaac aacgaacagt acgccagctc ttc                              33

<210> SEQ ID NO 7
<211> LENGTH: 34
<212> TYPE: DNA
<213> ORGANISM: Artificial
<220> FEATURE:
<223> OTHER INFORMATION: primer

<400> SEQUENCE: 7
cggagtgatg attcgtttta tcgtcaacaa gctg                             34

<210> SEQ ID NO 8
<211> LENGTH: 34
<212> TYPE: DNA
<213> ORGANISM: Artificial
<220> FEATURE:
<223> OTHER INFORMATION: primer

<400> SEQUENCE: 8
cagcttgttg acgataaaac gaatcatcac tccg                             34

<210> SEQ ID NO 9
<211> LENGTH: 34
<212> TYPE: DNA
<213> ORGANISM: Artificial
<220> FEATURE:
<223> OTHER INFORMATION: primer

<400> SEQUENCE: 9
cggagtgatg attcgtctga tcgtcaacaa gctg                             34

<210> SEQ ID NO 10
<211> LENGTH: 34
<212> TYPE: DNA
<213> ORGANISM: Artificial
<220> FEATURE:
<223> OTHER INFORMATION: primer

<400> SEQUENCE: 10
cagcttgttg acgataaaac gaatcatcac tccg   34

<210> SEQ ID NO 11
<211> LENGTH: 34
<212> TYPE: DNA
<213> ORGANISM: Artificial
<220> FEATURE:
<223> OTHER INFORMATION: primer

<400> SEQUENCE: 11
cggagtgatg attcgtatta tcgtcaacaa gctg   34

<210> SEQ ID NO 12
<211> LENGTH: 34
<212> TYPE: DNA
<213> ORGANISM: Artificial
<220> FEATURE:
<223> OTHER INFORMATION: primer

<400> SEQUENCE: 12
cagcttgttg acgataatac gaatcatcac tccg   34

<210> SEQ ID NO 13
<211> LENGTH: 34
<212> TYPE: DNA
<213> ORGANISM: Artificial
<220> FEATURE:
<223> OTHER INFORMATION: primer

<400> SEQUENCE: 13
cggagtgatg attcgtatga tcgtcaacaa gctg   34

<210> SEQ ID NO 14
<211> LENGTH: 34
<212> TYPE: DNA
<213> ORGANISM: Artificial
<220> FEATURE:
<223> OTHER INFORMATION: primer

<400> SEQUENCE: 14
cagcttgttg acgatcatac gaatcatcac tccg   34

<210> SEQ ID NO 15
<211> LENGTH: 34
<212> TYPE: DNA
<213> ORGANISM: Artificial
<220> FEATURE:
<223> OTHER INFORMATION: primer

<400> SEQUENCE: 15
cggagtgatg attcgtgtga tcgtcaacaa gctg   34

<210> SEQ ID NO 16
<211> LENGTH: 34
<212> TYPE: DNA
<213> ORGANISM: Artificial
<220> FEATURE:
<223> OTHER INFORMATION: primer

<400> SEQUENCE: 16
cagcttgttg acgatcacac gaatcatcac tccg   34

<210> SEQ ID NO 17
<211> LENGTH: 34
<212> TYPE: DNA
<213> ORGANISM: Artificial

```
<220> FEATURE:
<223> OTHER INFORMATION: primer

<400> SEQUENCE: 17
cggagtgatg attcgtgcga tcgtcaacaa gctg                              34

<210> SEQ ID NO 18
<211> LENGTH: 34
<212> TYPE: DNA
<213> ORGANISM: Artificial
<220> FEATURE:
<223> OTHER INFORMATION: primer

<400> SEQUENCE: 18
cagcttgttg acgatcgcac gaatcatcac tccg                              34

<210> SEQ ID NO 19
<211> LENGTH: 34
<212> TYPE: DNA
<213> ORGANISM: Artificial
<220> FEATURE:
<223> OTHER INFORMATION: primer

<400> SEQUENCE: 19
cggagtgatg attcgttata tcgtcaacaa gctg                              34

<210> SEQ ID NO 20
<211> LENGTH: 34
<212> TYPE: DNA
<213> ORGANISM: Artificial
<220> FEATURE:
<223> OTHER INFORMATION: primer

<400> SEQUENCE: 20
cagcttgttg acgatataac gaatcatcac tccg                              34

<210> SEQ ID NO 21
<211> LENGTH: 34
<212> TYPE: DNA
<213> ORGANISM: Artificial
<220> FEATURE:
<223> OTHER INFORMATION: primer

<400> SEQUENCE: 21
cggagtgatg attcgtcata tcgtcaacaa gctg                              34

<210> SEQ ID NO 22
<211> LENGTH: 34
<212> TYPE: DNA
<213> ORGANISM: Artificial
<220> FEATURE:
<223> OTHER INFORMATION: primer

<400> SEQUENCE: 22
cagcttgttg acgatatgac gaatcatcac tccg                              34

<210> SEQ ID NO 23
<211> LENGTH: 34
<212> TYPE: DNA
<213> ORGANISM: Artificial
<220> FEATURE:
<223> OTHER INFORMATION: primer

<400> SEQUENCE: 23
cggagtgatg attcgtcaga tcgtcaacaa gctg                              34
```

<210> SEQ ID NO 24
<211> LENGTH: 34
<212> TYPE: DNA
<213> ORGANISM: Artificial
<220> FEATURE:
<223> OTHER INFORMATION: primer

<400> SEQUENCE: 24
cagcttgttg acgatctgac gaatcatcac tccg                              34

<210> SEQ ID NO 25
<211> LENGTH: 34
<212> TYPE: DNA
<213> ORGANISM: Artificial
<220> FEATURE:
<223> OTHER INFORMATION: primer

<400> SEQUENCE: 25
cggagtgatg attcgtaaca tcgtcaacaa gctg                              34

<210> SEQ ID NO 26
<211> LENGTH: 34
<212> TYPE: DNA
<213> ORGANISM: Artificial
<220> FEATURE:
<223> OTHER INFORMATION: primer

<400> SEQUENCE: 26
cagcttgttg acgatgttac gaatcatcac tccg                              34

<210> SEQ ID NO 27
<211> LENGTH: 34
<212> TYPE: DNA
<213> ORGANISM: Artificial
<220> FEATURE:
<223> OTHER INFORMATION: primer

<400> SEQUENCE: 27
cggagtgatg attcgtaaaa tcgtcaacaa gctg                              34

<210> SEQ ID NO 28
<211> LENGTH: 34
<212> TYPE: DNA
<213> ORGANISM: Artificial
<220> FEATURE:
<223> OTHER INFORMATION: primer

<400> SEQUENCE: 28
cagcttgttg acgattttac gaatcatcac tccg                              34

<210> SEQ ID NO 29
<211> LENGTH: 34
<212> TYPE: DNA
<213> ORGANISM: Artificial
<220> FEATURE:
<223> OTHER INFORMATION: primer

<400> SEQUENCE: 29
cggagtgatg attcgtgata tcgtcaacaa gctg                              34

<210> SEQ ID NO 30
<211> LENGTH: 34
<212> TYPE: DNA
<213> ORGANISM: Artificial
<220> FEATURE:
<223> OTHER INFORMATION: primer

```
<400> SEQUENCE: 30
cagcttgttg acgatatcac gaatcatcac tccg                                34

<210> SEQ ID NO 31
<211> LENGTH: 34
<212> TYPE: DNA
<213> ORGANISM: Artificial
<220> FEATURE:
<223> OTHER INFORMATION: primer

<400> SEQUENCE: 31
cggagtgatg attcgtgaaa tcgtcaacaa gctg                                34

<210> SEQ ID NO 32
<211> LENGTH: 34
<212> TYPE: DNA
<213> ORGANISM: Artificial
<220> FEATURE:
<223> OTHER INFORMATION: primer

<400> SEQUENCE: 32
cagcttgttg acgatttcac gaatcatcac tccg                                34

<210> SEQ ID NO 33
<211> LENGTH: 34
<212> TYPE: DNA
<213> ORGANISM: Artificial
<220> FEATURE:
<223> OTHER INFORMATION: primer

<400> SEQUENCE: 33
cggagtgatg attcgttgga tcgtcaacaa gctg                                34

<210> SEQ ID NO 34
<211> LENGTH: 34
<212> TYPE: DNA
<213> ORGANISM: Artificial
<220> FEATURE:
<223> OTHER INFORMATION: primer

<400> SEQUENCE: 34
cagcttgttg acgatccaac gaatcatcac tccg                                34

<210> SEQ ID NO 35
<211> LENGTH: 34
<212> TYPE: DNA
<213> ORGANISM: Artificial
<220> FEATURE:
<223> OTHER INFORMATION: primer

<400> SEQUENCE: 35
cggagtgatg attcgtcgca tcgtcaacaa gctg                                34

<210> SEQ ID NO 36
<211> LENGTH: 34
<212> TYPE: DNA
<213> ORGANISM: Artificial
<220> FEATURE:
<223> OTHER INFORMATION: primer

<400> SEQUENCE: 36
cagcttgttg acgatgcgac gaatcatcac tccg                                34

<210> SEQ ID NO 37
```

```
<211> LENGTH: 34
<212> TYPE: DNA
<213> ORGANISM: Artificial
<220> FEATURE:
<223> OTHER INFORMATION: primer

<400> SEQUENCE: 37
cggagtgatg attcgtagca tcgtcaacaa gctg                              34

<210> SEQ ID NO 38
<211> LENGTH: 34
<212> TYPE: DNA
<213> ORGANISM: Artificial
<220> FEATURE:
<223> OTHER INFORMATION: primer

<400> SEQUENCE: 38
cagcttgttg acgatgctac gaatcatcac tccg                              34

<210> SEQ ID NO 39
<211> LENGTH: 32
<212> TYPE: DNA
<213> ORGANISM: Artificial
<220> FEATURE:
<223> OTHER INFORMATION: primer

<400> SEQUENCE: 39
gcacaacacg gtgcacatta tgcatccgat gc                                32

<210> SEQ ID NO 40
<211> LENGTH: 32
<212> TYPE: DNA
<213> ORGANISM: Artificial
<220> FEATURE:
<223> OTHER INFORMATION: primer

<400> SEQUENCE: 40
gcatcggatg cataatgtgc accgtgttgt gc                                32

<210> SEQ ID NO 41
<211> LENGTH: 29
<212> TYPE: DNA
<213> ORGANISM: Artificial
<220> FEATURE:
<223> OTHER INFORMATION: primer

<400> SEQUENCE: 41
gaacttcggt ggcacgtccg cctgtggcg                                    29

<210> SEQ ID NO 42
<211> LENGTH: 29
<212> TYPE: DNA
<213> ORGANISM: Artificial
<220> FEATURE:
<223> OTHER INFORMATION: primer

<400> SEQUENCE: 42
cgccacaggc ggacgtgcca ccgaagttc                                    29
```

MODIFIED AMINOTRANSFERASE, GENE THEREOF, AND METHOD FOR PRODUCING OPTICALLY ACTIVE AMINO COMPOUND USING SAME

CROSS REFERENCE TO RELATED APPLICATIONS

This application is a National Phase filing under 35 U.S.C. §371 of PCT/JP2012/056174 filed on Mar. 9, 2012; and this application claims priority to Application No. 2011-054636 filed in Japan on Mar. 11, 2011, under 35 U.S.C. §119; the entire contents of all are hereby incorporated by reference.

TECHNICAL FIELD

The invention relates to an enzyme capable of efficiently converting a ketone compound into an optically active amino compound via transamination and also to a method for producing an optically active amino compound using such an enzyme. The resulting optically active amino compound can be used as an intermediate for pharmaceuticals, agricultural chemicals, and other products.

BACKGROUND ART

Although many types of aminotransferases are known up to date, there are not so many reports on enzymes capable of producing optically active amino compounds other than α-amino acids (Non-Patent Document 1).

Thus, there are many problems with industrial applications of existing enzymes, such as insufficient stereoselectivity for desired compounds and low enzyme stability in reactions under temperature and pH conditions suitable for the physical properties of substrates.

Therefore, aminotransferases having high stereoselectivity and high stability in reactions for desired compounds, if available, would be useful for industrial production of optically active amino compounds.

PRIOR ART DOCUMENT

Non-Patent Document

Non-Patent Document 1: Trends in Biotechnology, 28, 324-332 (2010)

SUMMARY OF THE INVENTION

Problems to be Solved by the Invention

An object of the invention is to provide a modified aminotransferase having reactivity higher than that of the wild-type enzyme consisting of the amino acid sequence of SEQ ID NO: 1 in the Sequence Listing. Another object of the invention is to provide a method for efficiently producing an optically active amino compound from a ketone compound using such an enzyme or using a transformant capable of producing such an enzyme.

Means for Solving the Problems

As a result of various studies to achieve the objects, the inventors have accomplished the invention based on the finding that an aminotransferase having higher activity, stereoselectivity, and stability than the wild-type enzyme or showing lower product-induced inhibition than the wild-type enzyme can be obtained by introducing a mutation or mutations into an aminotransferase derived from Pseudomonas fluorescens strain KNK08-18 (a polypeptide consisting of the amino acid sequence of SEQ ID NO: 1). Specifically, the invention provides the following.

Item 1. A polypeptide having the following properties (i) to (iii):
  (i) having at least 85% sequence identity to an amino acid sequence of SEQ ID NO: 1;
  (ii) being capable of catalyzing a reaction of 7-methoxy-2-tetralone to produce (S)-7-methoxy-2-aminotetralin in the presence of an amino group donor; and
  (iii) having reactivity higher than that of an aminotransferase consisting of the amino acid sequence of SEQ ID NO: 1.

Item 2. A polypeptide selected from the group consisting of the following (A) to (C):
  (A) a polypeptide that consists of an amino acid sequence in which one or more amino acids have been substituted at one or more positions selected from positions 161, 420, 17, 84, 171, 176, 262, 302, 421, 435, 29, 42, 116, 153, 190, 284, 209, 235, 236, 408, 418, 434, 442, 3, 11, and 151 in the amino acid sequence of SEQ ID NO: 1;
  (B) a polypeptide that consists of an amino acid sequence in which one or more amino acids have been substituted at one or more positions selected from positions 161, 420, 17, 84, 171, 176, 262, 302, 421, 435, 29, 42, 116, 153, 190, 284, 209, 235, 236, 408, 418, 434, 442, 3, 11, and 151 and one or more amino acids at one or more positions other than the above amino acid positions in the amino acid sequence of SEQ ID NO: 1, and that is capable of catalyzing a reaction of 7-methoxy-2-tetralone to produce (S)-7-methoxy-2-aminotetralin in the presence of an amino group donor, and has reactivity higher than that of an aminotransferase consisting of the amino acid sequence of SEQ ID NO: 1; and
  (C) a polypeptide that consists of an amino acid sequence in which one or more amino acids have been substituted at one or more positions selected from positions 161, 420, 17, 84, 171, 176, 262, 302, 421, 435, 29, 42, 116, 153, 190, 284, 209, 235, 236, 408, 418, 434, 442, 3, 11, and 151 in the amino acid sequence of SEQ ID NO: 1, and a sequence identity to the amino acid sequence of SEQ ID NO: 1, except for the above substituted position or positions, is at least 85%, and that is capable of catalyzing a reaction of 7-methoxy-2-tetralone to produce (S)-7-methoxy-2-aminotetralin in the presence of an amino group donor, and has reactivity higher than that of an aminotransferase consisting of the amino acid sequence of SEQ ID NO: 1.

Item 3. The polypeptide according to item 1 or 2, which has one or more amino acid substitutions selected from the group consisting of:
a substitution of an uncharged amino acid or a nonpolar amino acid for a residue at position 161 in the amino acid sequence of SEQ ID NO: 1;
a substitution of an amino acid other than proline, glycine, cysteine, and threonine for a residue at position 420 in the amino acid sequence of SEQ ID NO: 1;
a substitution of a nonpolar amino acid for a residue at position 17 in the amino acid sequence of SEQ ID NO: 1;
a substitution of an uncharged amino acid for a residue at position 84 in the amino acid sequence of SEQ ID NO: 1;
a substitution of a basic amino acid for a residue at position 171 in the amino acid sequence of SEQ ID NO: 1;
a substitution of an uncharged amino acid for a residue at position 176 in the amino acid sequence of SEQ ID NO: 1;
a substitution of a nonpolar amino acid for a residue at position 262 in the amino acid sequence of SEQ ID NO: 1;

a substitution of a nonpolar amino acid for a residue at position 302 in the amino acid sequence of SEQ ID NO: 1;
a substitution of an uncharged amino acid for a residue at position 421 in the amino acid sequence of SEQ ID NO: 1;
a substitution of a nonpolar amino acid for a residue at position 435 in the amino acid sequence of SEQ ID NO: 1;
a substitution of a basic amino acid for a residue at position 29 in the amino acid sequence of SEQ ID NO: 1;
a substitution of an uncharged amino acid for a residue at position 42 in the amino acid sequence of SEQ ID NO: 1;
a substitution of a nonpolar amino acid for a residue at position 116 in the amino acid sequence of SEQ ID NO: 1;
a substitution of a nonpolar amino acid for a residue at position 153 in the amino acid sequence of SEQ ID NO: 1;
a substitution of a nonpolar amino acid for a residue at position 190 in the amino acid sequence of SEQ ID NO: 1;
a substitution of an uncharged amino acid for a residue at position 284 in the amino acid sequence of SEQ ID NO: 1;
a substitution of a nonpolar amino acid for a residue at position 209 in the amino acid sequence of SEQ ID NO: 1;
a substitution of a nonpolar amino acid for a residue at position 235 in the amino acid sequence of SEQ ID NO: 1;
a substitution of a nonpolar amino acid for a residue at position 236 in the amino acid sequence of SEQ ID NO: 1;
a substitution of an uncharged amino acid for a residue at position 408 in the amino acid sequence of SEQ ID NO: 1;
a substitution of an uncharged amino acid for a residue at position 418 in the amino acid sequence of SEQ ID NO: 1;
a substitution of a nonpolar amino acid for a residue at position 434 in the amino acid sequence of SEQ ID NO: 1;
a substitution of a nonpolar amino acid for a residue at position 442 in the amino acid sequence of SEQ ID NO: 1;
a substitution of a basic amino acid for a residue at position 3 in the amino acid sequence of SEQ ID NO: 1;
a substitution of an uncharged amino acid for a residue at position 11 in the amino acid sequence of SEQ ID NO: 1; and
a substitution of a basic amino acid for a residue at position 151 in the amino acid sequence of SEQ ID NO: 1.

Item 4. The polypeptide according to item 1 or 2, which has one or more amino acid substitutions selected from the group consisting of:
a substitution of threonine or valine for a residue at position 161 in the amino acid sequence of SEQ ID NO: 1;
a substitution of histidine, serine, alanine, aspartic acid, glutamic acid, arginine, glutamine, asparagine, lysine, valine, or tryptophan for a residue at position 420 in the amino acid sequence of SEQ ID NO: 1;
a substitution of isoleucine or leucine for a residue at position 17 in the amino acid sequence of SEQ ID NO: 1;
a substitution of cysteine for a residue at position 84 in the amino acid sequence of SEQ ID NO: 1;
a substitution of arginine for a residue at position 171 in the amino acid sequence of SEQ ID NO: 1;
a substitution of serine for a residue at position 176 in the amino acid sequence of SEQ ID NO: 1;
a substitution of valine for a residue at position 262 in the amino acid sequence of SEQ ID NO: 1;
a substitution of isoleucine for a residue at position 302 in the amino acid sequence of SEQ ID NO: 1;
a substitution of threonine for a residue at position 421 in the amino acid sequence of SEQ ID NO: 1;
a substitution of alanine for a residue at position 435 in the amino acid sequence of SEQ ID NO: 1;
a substitution of lysine for a residue at position 29 in the amino acid sequence of SEQ ID NO: 1;
a substitution of tyrosine for a residue at position 42 in the amino acid sequence of SEQ ID NO: 1;
a substitution of leucine for a residue at position 116 in the amino acid sequence of SEQ ID NO: 1;
a substitution of phenylalanine for a residue at position 153 in the amino acid sequence of SEQ ID NO: 1;
a substitution of tyrosine for a residue at position 190 in the amino acid sequence of SEQ ID NO: 1;
a substitution of isoleucine for a residue at position 284 in the amino acid sequence of SEQ ID NO: 1;
a substitution of alanine for a residue at position 209 in the amino acid sequence of SEQ ID NO: 1;
a substitution of valine for a residue at position 235 in the amino acid sequence of SEQ ID NO: 1;
a substitution of isoleucine for a residue at position 236 in the amino acid sequence of SEQ ID NO: 1;
a substitution of threonine for a residue at position 408 in the amino acid sequence of SEQ ID NO: 1;
a substitution of leucine for a residue at position 418 in the amino acid sequence of SEQ ID NO: 1;
a substitution of alanine for a residue at position 434 in the amino acid sequence of SEQ ID NO: 1;
a substitution of valine for a residue at position 442 in the amino acid sequence of SEQ ID NO: 1;
a substitution of arginine for a residue at position 3 in the amino acid sequence of SEQ ID NO: 1;
a substitution of glycine for a residue at position 11 in the amino acid sequence of SEQ ID NO: 1; and
a substitution of histidine for a residue at position 151 in the amino acid sequence of SEQ ID NO: 1.

Item 5. The polypeptide according to item 1 or 2, which has amino acid substitutions of at least one type selected from the group consisting of the following types (1) to (15):

(1) a substitution of an uncharged amino acid for a residue at position 161, a substitution of a nonpolar amino acid for a residue at position 17, and a substitution of histidine, serine, alanine, aspartic acid, or glutamic acid for a residue at position 420 in the amino acid sequence of SEQ ID NO: 1;

(2) a substitution of an uncharged amino acid for a residue at position 161 and a substitution of an uncharged amino acid for a residue at position 418 in the amino acid sequence of SEQ ID NO: 1;

(3) a substitution of an uncharged amino acid for a residue at position 161, a substitution of a nonpolar amino acid for a residue at position 236, and a substitution of a nonpolar amino acid for a residue at position 442 in the amino acid sequence of SEQ ID NO: 1;

(4) a substitution of an uncharged amino acid for a residue at position 161 and a substitution of a nonpolar amino acid for a residue at position 434 in the amino acid sequence of SEQ ID NO: 1;

(5) a substitution of an uncharged amino acid for a residue at position 11, a substitution of a basic amino acid for a residue at position 151, a substitution of an uncharged amino acid for a residue at position 161, and a substitution of a nonpolar amino acid, preferably valine, for a residue at position 262 in the amino acid sequence of SEQ ID NO: 1;

(6) a substitution of an uncharged amino acid for a residue at position 161, a substitution of a nonpolar amino acid for a residue at position 209, and a substitution of a nonpolar amino acid for a residue at position 235 of in the amino acid sequence SEQ ID NO: 1;

(7) a substitution of an uncharged amino acid for a residue at position 42 and a substitution of an uncharged amino acid for a residue at position 408 in the amino acid sequence of SEQ ID NO: 1:

(8) a substitution of a nonpolar amino acid for a residue at position 17 and a substitution of a nonpolar amino acid for a residue at position 153 in the amino acid sequence of SEQ ID NO: 1;

(9) a substitution of a basic amino acid for a residue at position 29 and a substitution of a nonpolar amino acid for a residue at position 262 in the amino acid sequence of SEQ ID NO: 1;

(10) a substitution of an uncharged amino acid for a residue at position 161 and a substitution of an uncharged amino acid for a residue at position 284 in the amino acid sequence of SEQ ID NO: 1;

(11) a substitution of a basic amino acid for a residue at position 3, a substitution of a nonpolar amino acid for a residue at position 17, a substitution of a nonpolar amino acid for a residue at position 116, and a substitution of a nonpolar amino acid for a residue at position 190 in the amino acid sequence of SEQ ID NO: 1;

(12) a substitution of an uncharged amino acid for a residue at position 84 and a substitution of an uncharged amino acid other than threonine for a residue at position 420 in the amino acid sequence of SEQ ID NO: 1;

(13) a substitution of an uncharged amino acid for a residue at position 161 and a substitution of a nonpolar amino acid for a residue at position 17 in the amino acid sequence of SEQ ID NO: 1;

(14) a substitution of an uncharged amino acid for a residue at position 161 and a substitution of a basic amino acid for a residue at position 420 in the amino acid sequence of SEQ ID NO: 1; and

(15) a substitution of a nonpolar amino acid for a residue at position 17 and a substitution of a basic amino acid for a residue at position 420 in the amino acid sequence of SEQ ID NO: 1.

Item 6. The polypeptide according to item 1 or 2, which has amino acid substitutions of at least one type selected from the group consisting of the following types (16) to (30):

(16) a substitution of isoleucine for a residue at position 17, a substitution of threonine for a residue at position 161, and a substitution of histidine for a residue at position 420 in the amino acid sequence of SEQ ID NO: 1;

(17) a substitution of threonine for a residue at position 161 and a substitution of leucine for a residue at position 418 in the amino acid sequence of SEQ ID NO: 1;

(18) a substitution of threonine for a residue at position 161, a substitution of isoleucine for a residue at position 236, and a substitution of valine for a residue at position 442 in the amino acid sequence of SEQ ID NO: 1;

(19) a substitution of threonine for a residue at position 161 and a substitution of alanine for a residue at position 434 in the amino acid sequence of SEQ ID NO: 1;

(20) a substitution of glycine for a residue at position 11, a substitution of histidine for a residue at position 151, a substitution of threonine for a residue at position 161, and a substitution of valine for a residue at position 262 in the amino acid sequence of SEQ ID NO: 1;

(21) a substitution of threonine for a residue at position 161, a substitution of alanine for a residue at position 209, and a substitution of valine for a residue at position 235 in the amino acid sequence of SEQ ID NO: 1;

(22) a substitution of tyrosine for a residue at position 42 and a substitution of threonine for a residue at position 408 in the amino acid sequence of SEQ ID NO: 1;

(23) a substitution of leucine for a residue at position 17 and a substitution of phenylalanine for a residue at position 153 in the amino acid sequence of SEQ ID NO: 1;

(24) a substitution of lysine for a residue at position 29 and a substitution of valine for a residue at position 262 in the amino acid sequence of SEQ ID NO: 1;

(25) a substitution of threonine for a residue at position 161 and a substitution of isoleucine for a residue at position 284 in the amino acid sequence of SEQ ID NO: 1;

(26) a substitution of arginine for a residue at position 3, a substitution of leucine for a residue at position 17, a substitution of leucine for a residue at position 116, and a substitution of tyrosine for a residue at position 190 in the amino acid sequence of SEQ ID NO: 1;

(27) a substitution of cysteine for a residue at position 84 and a substitution of serine for a residue at position 420 in the amino acid sequence of SEQ ID NO: 1;

(28) a substitution of isoleucine for a residue at position 17 and a substitution of threonine for a residue at position 161 in the amino acid sequence of SEQ ID NO: 1;

(29) a substitution of threonine for a residue at position 161 and a substitution of histidine for a residue at position 420 in the amino acid sequence of SEQ ID NO: 1; and

(30) a substitution of isoleucine for a residue at position 17 and a substitution of histidine for a residue at position 420 in the amino acid sequence of SEQ ID NO: 1.

Item 7. An isolated DNA encoding the polypeptide according to any one of items 1 to 6.

Item 8. A vector including the DNA according to item 7.

Item 9. A transformant obtained by transforming a host cell with the vector according to item 8.

Item 10. A method for producing an optically active amino compound, the method comprising allowing a ketone compound to react, in the presence of an amino group donor, with the polypeptide according to any one of items 1 to 6 or the transformant according to item 9, and/or a processed product therefrom.

Item 11. The method according to item 8, wherein the ketone compound is an unsymmetrical ketone represented by the following formula (1):

wherein $R^1$ and $R^2$ each represent an optionally substituted alkyl group, an optionally substituted aralkyl group, or an optionally substituted aryl group, and $R^1$ and $R^2$ may be linked together to form a ring, provided that $R^1$ and $R^2$ have different structures, and a product of the reaction is an optically active amino compound represented by the following formula (2):

wherein $R^1$ and $R^2$ have the same meanings as in the formula (1), and * indicates an asymmetric carbon atom.

Item 12. A method for producing an optically active amino compound, the method comprising allowing an enantiomeric mixture of amino compounds to react, in the presence of an amino group acceptor, with the polypeptide according to any one of items 1 to 6 or the transformant according to item 9, and/or a processed product therefrom.

Item 13. The method according to item 12, wherein the amino compounds form an enantiomeric mixture represented by the following formula (3):

(3)

wherein $R^1$ and $R^2$ each represent an optionally substituted alkyl group, an optionally substituted aralkyl group, or an optionally substituted aryl group, and $R^1$ and $R^2$ may be linked together to form a ring, provided that $R^1$ and $R^2$ have different structures, and a product of the reaction is an optically active amino compound represented by the following formula (4):

(4)

wherein $R^1$ and $R^2$ have the same meanings as in the formula (3), and * indicates an asymmetric carbon atom.

Item 14. The method according to item 11, wherein the ketone compound represented by formula (1) is at least one ketone compound selected from the group consisting of 1-tetralone, 2-tetralone, 5-methoxy-2-tetralone, 6-methoxy-2-tetralone, 7-methoxy-2-tetralone, 8-methoxy-2-tetralone, 1-benzyl-3-pyrrolidinone, 1-Boc-3-pyrrolidinone, 1-Cbz-3-pyrrolidinone, 1-benzyl-3-piperidinone, 1-Boc-3-piperidinone, 1-Cbz-3-piperidinone, acetophenone, and 3,4-dimethoxyphenylacetone.

Item 15. The method according to item 13, wherein the amino compound represented by formula (3) is at least one amino compound selected from the group consisting of 1-aminotetralin, 2-aminotetralin, 5-methoxy-2-aminotetralin, 6-methoxy-2-aminotetralin, 7-methoxy-2-aminotetralin, 8-methoxy-2-aminotetralin, 1-benzyl-3-aminopyrrolidine, 1-Boc-3-aminopyrrolidine, 1-Cbz-3-aminopyrrolidine, 1-benzyl-3-aminopiperidine, 1-Boc-3-aminopiperidine, 1-Cbz-3-aminopiperidine, 1-phenethylamine, and 3,4-dimethoxyamphetamine.

Item 16. The method according to item 10, 11 or 14, wherein the amino group donor is at least one compound selected from the group consisting of 1-phenethylamine, 2-butylamine, 2-pentylamine, 2-heptylamine, 3-heptylamine, n-ethylamine, n-propylamine, n-butylamine, n-amylamine, isopropylamine, isobutylamine, glycine, alanine, glutamic acid, 3-amino-1-phenylbutane, benzylamine, β-phenethylamine, cyclohexylamine, and optically active compounds thereof Item 17. The method according to item 12 or 13, wherein the amino group acceptor is pyruvic acid or glyoxylic acid.

Item 18. The method according to any one of items 10 to 17, further comprising keeping the reaction at a temperature of at least 35° C.

Effect of the Invention

A modified aminotransferase having higher activity, stereoselectivity, and stability or showing lower product-induced inhibition is successfully obtained by modifying the amino acid sequence of an aminotransferase derived from *Pseudomonas fluorescens* strain KNK08-18. The use of the modified aminotransferase enables efficient production of optically active amino compounds.

MODE FOR CARRYING OUT THE INVENTION

Hereinafter, the invention will be described in detail. Unless otherwise stated, genetic manipulations such as isolation of DNA, preparation of vectors, and transformation can be performed according to textbooks such as Molecular Cloning 2nd Edition (Cold Spring Harbor Laboratory Press, 1989), and Current Protocols in Molecular Biology (Greene Publishing Associates and Wiley-Interscience).

In the description, the abbreviations shown below are used to indicate amino acids, peptides, and proteins as recommended by the IUPAC-IUB Biochemical Nomenclature Committee (CBN). Unless otherwise specified, the sequence of amino acid residues in peptides or proteins is written with the N-terminus to the left and the C-terminus to the right. To make reference easy, the commonly used nomenclature shown below is used. One is the following nomenclature: "original amino acid; position; substituted amino acid". Accordingly, for example, the substitution of tyrosine at position 64 with aspartic acid is designated as "Tyr64Asp" or "Y64D". Multiple mutations are separated by addition of slash marks "/". For example, S41A/Y64D represents substitutions at positions 41 and 64 of serine with alanine and tyrosine with aspartic acid, respectively.

A=Ala=alanine, C=Cys=cysteine,
D=Asp=aspartic acid, E=Glu=glutamic acid,
F=Phe=phenylalanine, G=Gly=glycine,
H=His=histidine, I=Ile=isoleucine,
K=Lys=lysine, L=Leu=leucine,
M=Met=methionine, N=Asn=asparagine,
P=Pro=proline, Q=Gln=glutamine,
R=Arg=arginine, S=Ser=serine,
T=Thr=threonine, V=Val=valine,
W=Trp=tryptophan, Y=Tyr=tyrosine As used herein, the term "nonpolar amino acid" is intended to include alanine, valine, leucine, isoleucine, proline, methionine, phenylalanine, and tryptophan, the term "uncharged amino acid" is intended to include glycine, serine, threonine, cysteine, tyrosine, asparagine, and glutamine, the term "acidic amino acid" is intended to include aspartic acid and glutamic acid, and the term "basic amino acid" is intended to include lysine, arginine, and histidine.

Concerning units for enzyme activity, unless otherwise specified, 1 U is defined as the amount of enzyme required to form 1 μmol of a product for 1 minute.

1. Wild-Type Enzyme and its Gene

In the invention, the wild-type enzyme without any mutation has 454 amino acid residues represented by SEQ ID NO: 1 in the Sequence Listing, which is a polypeptide having the ability to produce an optically active amino compound from a ketone compound (e.g., to produce (S)-7-methoxy-2-aminotetralin from 7-methoxy-2-tetralone) in the presence of an amino group donor. This polypeptide is expressed as the wild-type enzyme.

Although the source of the polypeptide is not restricted, the polypeptide is preferably an aminotransferase derived from microorganisms belonging to *Pseudomonas* genus, more preferably from *Pseudomonas fluorescens*, even more preferably from *Pseudomonas fluorescens* strain KNK08-18. This strain is deposited as Accession Number FERM P-20239 on Oct. 5, 2004 in The National Institute of Advanced Industrial Science and Technology, International Patent Organism Depositary (Tsukuba Central 6, 1-1-1 Higashi, Tsukuba, Ibaraki, 305-8566 Japan).

The gene of the wild-type enzyme according to the invention is the polynucleotide represented by SEQ ID NO: 2 in the Sequence Listing, which can be obtained from *Pseudomonas* genus, preferably *Pseudomonas fluorescens* strain KNK08-18 using common genetic engineering techniques described in publications such as Molecular Cloning 2nd Edition (Joseph Sambrook, Cold Spring Harbor Laboratory Press (1989)).

Specifically, the wild-type gene can be prepared by performing PCR using genomic DNA from *Pseudomonas fluorescens* strain KNK08-18 to amplify DNA according to the method described in WO 2006/126498 A1, in which the DNA consists of a base sequence encoding the amino acid sequence of SEQ ID NO: 1 in the Sequence Listing or has the base sequence of SEQ ID NO: 2 in the Sequence Listing.

Alternatively, organic chemical synthesis techniques may be used to obtain the wild-type gene such as DNA consisting of a base sequence encoding the amino acid sequence of SEQ ID NO: 1 in the Sequence Listing or DNA having the base sequence of SEQ ID NO: 2 in the Sequence Listing.

2. Modified Aminotransferase

An aspect of the polypeptide of the invention includes a polypeptide that has at least 85% sequence identity to the amino acid sequence of SEQ ID NO: 1 in the Sequence Listing, is capable of catalyzing a reaction to produce (S)-7-methoxy-2-aminotetralin from 7-methoxy-2-tetralone in the presence of an amino group donor, and has reactivity higher than the wild-type enzyme.

As used herein, the phrase "has reactivity higher than" means that at least one of the properties (a) to (e) below is satisfied in comparison with the wild-type enzyme.

(a) Stereoselectivity for 7-methoxy-2-tetralone is higher.
(b) Thermal stability is higher.
(c) Stability in the presence of (S)-7-methoxy-2-aminotetralin is higher.
(d) Activity to 7-methoxy-2-tetralone is higher.
(e) (S)-7-methoxy-2-aminotetralin-induced competitive inhibition is reduced.

The term "wild-type enzyme" means an aminotransferase consisting of the amino acid sequence of SEQ ID NO: 1 in the Sequence Listing.

The polypeptide of the invention may also be obtained by modifying the amino acid sequence of SEQ ID NO: 1 in the Sequence Listing. The "modified aminotransferase" is preferably a polypeptide having an amino acid sequence modified by substitution, addition, insertion, or deletion of one or more or a few amino acids in the amino acid sequence of SEQ ID NO: 1 in the Sequence Listing and having at least 85% sequence identity to the aminotransferase of the amino acid sequence of SEQ ID NO: 1 in the Sequence Listing. One or more or a few amino acids may also be added to one or both of the N- and C-termini of such a polypeptide.

Modifications to the amino acid sequence of SEQ ID NO: 1 in the Sequence Listing include substitution, addition, insertion, or deletion, and may include a single type of modification (e.g., substitution) or two or more types of modifications (e.g., substitution and insertion). The term "more amino acids" typically means 70, preferably 50, more preferably 20, even more preferably 10, 8, 5, 4, 3, or 2 amino acids.

The modified amino acid sequence has at least 85%, preferably at least 90%, more preferably at least 95%, even more preferably at least 96%, still more preferably at least 97%, further more preferably at least 98%, most preferably at least 99% sequence identity to the amino acid sequence of SEQ ID NO: 1 in the Sequence Listing.

When the aminotransferase modified by adding one or more amino acids to one or both of the N- and C-termini is evaluated for sequence identity, such additional amino acids shall be excluded from the evaluation.

As used herein, the term "sequence identity" for polypeptides and polynucleotides refers to the value obtained by optimally aligning two polypeptides or polynucleotides to be compared, counting the number of positions of amino acids or nucleic acid bases (e.g., A, T, C, G, U, or I) matched between both sequences, dividing the counted number by the total number of the compared amino acids or bases, and multiplying the result of the division by 100.

When any other enzyme, protein, or peptide is added to express the aminotransferase, such additional parts shall be excluded in the determination of the sequence identity.

More specifically, the polypeptide or polynucleotide sequence identity can be determined by Maximum matching program with default parameters using GENETYX Ver. 10 (GENETYX CORPORATION).

The amino acid sequence of SEQ ID NO: 1 in the Sequence Listing may be modified by amino acid substitution, insertion, deletion, or addition at any position(s). In view of an improvement in reactivity, the polypeptide preferably has an amino acid sequence derived from the amino acid sequence of SEQ ID NO: 1 in the Sequence Listing by substitution of one or more amino acids at one or more positions selected from positions 3, 11, 17, 29, 42, 84, 116, 151, 153, 161, 171, 176, 190, 284, 209, 235, 236, 262, 302, 408, 418, 420, 421, 434, 435, and 442 of SEQ ID NO: 1 or by addition of one or more amino acids to one or both of the N- and C-termini of the amino acid sequence.

A preferred aspect of the polypeptide of the invention is any one of the polypeptides (A) to (C) shown below.

(A) A polypeptide that consists of an amino acid sequence in which one or more amino acids have been substituted at one or more positions selected from positions 3, 11, 17, 29, 42, 84, 116, 151, 153, 161, 171, 176, 190, 284, 209, 235, 236, 262, 302, 408, 418, 420, 421, 434, 435, and 442 in the amino acid sequence of SEQ ID NO: 1.

(B) A polypeptide that consists of an amino acid sequence in which one or more amino acids have been substituted at one or more positions selected from positions 3, 11, 17, 29, 42, 84, 116, 151, 153, 161, 171, 176, 190, 284, 209, 235, 236, 262, 302, 408, 418, 420, 421, 434, 435, and 442, and one or more amino acids at one or more positions other than the above amino acid positions in the amino acid sequence of SEQ ID NO: 1, and that is capable of catalyzing a reaction of 7-methoxy-2-tetralone to produce (S)-7-methoxy-2-aminotetralin in the presence of an amino group donor, and has reactivity higher than that of an aminotransferase consisting of the amino acid sequence of SEQ ID NO: 1.

(C) A polypeptide that consists of an amino acid sequence in which one or more amino acids have been substituted at one or more positions selected from positions 3, 11, 17, 29, 42, 84, 116, 151, 153, 161, 171, 176, 190, 284, 209, 235, 236, 262, 302, 408, 418, 420, 421, 434, 435, and 442 in the amino acid sequence of SEQ ID NO: 1, and a sequence identity to the amino acid sequence of SEQ ID NO: 1, except for the above substituted position or positions, is at least 85%, and that is capable of catalyzing a reaction of 7-methoxy-2-tetralone to produce (S)-7-methoxy-2-aminotetralin in the presence of an amino group donor, and has reactivity higher than that of an aminotransferase consisting of the amino acid sequence of SEQ ID NO: 1.

Hereinafter, concerning the polypeptides (B) and (C), amino acid positions other than positions 3, 11, 17, 29, 42, 84, 116, 151, 153, 161, 171, 176, 190, 284, 209, 235, 236, 262, 302, 408, 418, 420, 421, 434, 435, and 442 of SEQ ID NO: 1 in the Sequence Listing are also referred to as "optional modification positions."

Concerning the polypeptides (B) and (C), the phrase "has reactivity higher than" means that the polypeptide has at least one of the properties (a) to (e) stated above, and preferably means that the polypeptide has at least one of the properties (f) to (j) below in comparison with the polypeptide prior to the substitution, addition, insertion, or deletion at any of the optional modification positions.

(f) Stereoselectivity for 7-methoxy-2-tetralone is equal or higher.

(g) Thermal stability is equal or higher.

(h) Stability in the presence of (S)-7-methoxy-2-aminotetralin is equal or higher.

(i) Activity to 7-methoxy-2-tetralone is equal or higher.

(j) The effect of reducing (S)-7-methoxy-2-aminotetralin-induced competitive inhibition is equal or higher.

Among substitution, addition, insertion, and deletion for amino acid modification, a single type of modification (e.g., substitution) or two or more types of modifications (e.g., substitution and insertion) may be introduced into any of the optional modification positions when the polypeptide (B) is formed. In the polypeptide (B), one or more or a few amino acids may be substituted, added, inserted, or deleted at any of the optional modification positions, and the number of such modified amino acids is typically 1 to 70, preferably 1 to 50, more preferably 1 to 20, even more preferably 1 to 10, 1 to 8, 1 to 5, 1 to 4, 1 to 3, or 1 or 2.

Concerning the polypeptide (C), the term "sequence identity to the amino acid sequence of SEQ ID NO: 1 in the Sequence Listing, except for the substituted position or positions" refers to the sequence identity that is determined by extracting the optional modification positions from the amino acid sequence of SEQ ID NO: 1 in the Sequence Listing and comparing only the optional modification positions with the reference sequence. The method of determining the sequence identity may be as described above.

Concerning the polypeptide (C), "Sequence identity to the amino acid sequence of SEQ ID NO: 1, except for the substituted position or positions" is at least 85%, preferably at least 90%, more preferably at least 95%, even more preferably at least 96%, still more preferably at least 97%, further more preferably at least 98%, most preferably at least 99%.

In general, to conserve the function of polypeptides, it is preferred that amino acids should be substituted by other amino acids having similar properties. Such amino acid residue substitution is called conservative substitution. Amino acid substitution introduced into the optional modification positions of the polypeptides (B) and (C) is preferably conservative substitution. Specifically, examples of substitution at the optional substitution positions include substitution of nonpolar amino acids by other nonpolar amino acids, substitution of uncharged amino acids by other uncharged amino acids, substitution of acidic amino acids by other acidic amino acids, and substitution of basic amino acids by other basic amino acids.

In the optional modification positions of the polypeptides (B) and (C), amino acids are preferably substituted, inserted, or deleted at positions excluding the highly conserved regions of the aminotransferase having the amino acid sequence of SEQ ID NO: 1 in the Sequence Listing. The highly conserved regions refer to positions at which amino acid residues are identical between two or more different sequences when the amino acid sequences of two or more enzymes having different sources are optimally aligned and compared. The highly conserved regions can be identified by comparing the amino acid sequence of SEQ ID NO: 1 in the Sequence Listing and the base sequences of known aminotransferase genes derived from microorganisms using a tool such as GENETYX. For example, the highly conserved regions include the amino acids at positions 38, 139, 162, 212, 221, 226, 230, 231, 232, 237, 241, 259, 260, 261, 264, 266, 267, 269, 273, 281, 282, 288, 296, 299, 325, 328, 329, 330, 331, 334, 346, 378, 380, and 388 of the amino acid sequence of SEQ ID NO: 1 in the Sequence Listing. In particular, the amino acids at positions 288, 259, 121, 261, and 325 of the amino acid sequence of SEQ ID NO: 1 in the Sequence Listing are considered to form the active center of the aminotransferase (FEBS journal (doi: 10.11111/j.1742-4658.2011.08468.x); Biotechnology and Bioengineering 99(2), 275-284, 2008), and such amino acids are preferably conserved without being subjected to substitution, insertion, or deletion.

(Reactivity Improvement)

The peptide of the invention may have any amino acid substitution for the residue at any one of positions 3, 11, 17, 29, 42, 84, 116, 151, 153, 161, 171, 176, 190, 284, 209, 235, 236, 262, 302, 408, 418, 420, 421, 434, 435, and 442 in the amino acid sequence of SEQ ID NO: 1. In view of reactivity improvement, however, the polypeptide of the invention preferably has one or more of amino acid substitutions (1a) to (26a) shown below.

(1a) a substitution of preferably a basic amino acid, more preferably arginine, for the residue at position 3;

(2a) a substitution of preferably an uncharged amino acid, more preferably glycine, for the residue at position 11;

(3a) a substitution of preferably a nonpolar amino acid, more preferably isoleucine or leucine, even more preferably isoleucine, for the residue at position 17;

(4a) a substitution of preferably a basic amino acid, more preferably lysine, for the residue at position 29;

(5a) a substitution of preferably an uncharged amino acid, more preferably tyrosine, for the residue at position 42;

(6a) a substitution of preferably an uncharged amino acid, more preferably cysteine, for the residue at position 84;

(7a) a substitution of preferably a nonpolar amino acid, more preferably leucine, for the residue at position 116;

(8a) a substitution of preferably a basic amino acid, more preferably histidine, for the residue at position 151;

(9a) a substitution of preferably a nonpolar amino acid, more preferably phenylalanine, for the residue at position 153;

(10a) a substitution of preferably an uncharged amino acid or a nonpolar amino acid, more preferably an uncharged amino acid, even more preferably threonine or valine, for the residue at position 161;

(11a) a substitution of preferably a basic amino acid, more preferably arginine, for the residue at position 171;

(12a) a substitution of preferably an uncharged amino acid, more preferably serine, for the residue at position 176;

(13a) a substitution of preferably an uncharged amino acid, more preferably isoleucine, for the residue at position 284;

(14a) a substitution of preferably a nonpolar amino acid, more preferably tyrosine, for the residue at position 190;

(15a) a substitution of preferably a nonpolar amino acid, more preferably alanine, for the residue at position 209;

(16a) a substitution of preferably a nonpolar amino acid, more preferably valine, for the residue at position 235;

(17a) a substitution of preferably a nonpolar amino acid, more preferably isoleucine, for the residue at position 236;

(18a) a substitution of preferably a nonpolar amino acid, more preferably valine, for the residue at position 262;

(19a) a substitution of preferably a nonpolar amino acid, more preferably isoleucine, for the residue at position 302;

(20a) a substitution of preferably an uncharged amino acid, more preferably threonine, for the residue at position 408;

(21a) a substitution of preferably an uncharged amino acid, more preferably leucine, for the residue at position 418;

(22a) a substitution of preferably an amino acid other than proline, glycine, cysteine, and threonine, more preferably aspartic acid, glutamic acid, arginine, histidine, glutamine, asparagine, lysine, alanine, valine, tryptophan, or serine, even more preferably alanine, serine, histidine, aspartic acid, or glutamic acid, still more preferably alanine, serine, or histidine, most preferably histidine, for the residue at position 420;

(23a) a substitution of preferably an uncharged amino acid, more preferably threonine, for the residue at position 421;

(24a) a substitution of preferably a nonpolar amino acid, more preferably alanine, for the residue at position 434;

(25a) a substitution of preferably a nonpolar amino acid, more preferably alanine, for the residue at position 435;

(26a) a substitution of preferably a nonpolar amino acid, more preferably valine, for the residue at position 442.

(a) Stereoselectivity for 7-Methoxy-2-Tetralone

In view of stereoselectivity improvement, the polypeptide preferably has one or more substitutions for the amino acid residue or residues at one or more positions selected from positions 11, 17, 29, 42, 84, 151, 161, 176, 284, 209, 235, 236, 262, 408, 418, 420, 421, 434, and 442 in the amino acid sequence of SEQ ID NO: 1 in the Sequence Listing, or preferably has one or more amino acid residues added to one or both of the N- and C-termini of the amino acid sequence having said substitution(s).

More preferably, the polypeptide has one or more amino acid substitutions selected from the group consisting of the following types (1b) to (19b):

(1b) a substitution of an uncharged amino acid, preferably glycine, for the residue at position 11 in the amino acid sequence of SEQ ID NO: 1;

(2b) a substitution of a nonpolar amino acid, preferably isoleucine or leucine, more preferably isoleucine, for the residue at position 17 in the amino acid sequence of SEQ ID NO: 1;

(3b) a substitution of a basic amino acid, preferably lysine, for the residue at position 29 in the amino acid sequence of SEQ ID NO: 1;

(4b) a substitution of an uncharged amino acid, preferably tyrosine, for the residue at position 42 in the amino acid sequence of SEQ ID NO: 1;

(5b) a substitution of an uncharged amino acid, preferably cysteine, for the residue at position 84 in the amino acid sequence of SEQ ID NO: 1;

(6b) a substitution of a basic amino acid, preferably histidine, for the residue at position 151 in the amino acid sequence of SEQ ID NO: 1;

(7b) a substitution of an uncharged amino acid or a nonpolar amino acid, preferably threonine or valine, for the residue at position 161 in the amino acid sequence of SEQ ID NO: 1;

(8b) a substitution of an uncharged amino acid, preferably serine, for the residue at position 176 in the amino acid sequence of SEQ ID NO: 1;

(9b) a substitution of an uncharged amino acid, preferably isoleucine, for the residue at position 284 in the amino acid sequence of SEQ ID NO: 1;

(10b) a substitution of a nonpolar amino acid, preferably alanine, for the residue at position 209 in the amino acid sequence of SEQ ID NO: 1;

(11b) a substitution of a nonpolar amino acid, preferably valine, for the residue at position 235 in the amino acid sequence of SEQ ID NO: 1;

(12b) a substitution of a nonpolar amino acid, preferably isoleucine, for the residue at position 236 in the amino acid sequence of SEQ ID NO: 1;

(13b) a substitution of a nonpolar amino acid, preferably valine, for the residue at position 262 in the amino acid sequence of SEQ ID NO: 1;

(14b) a substitution of an uncharged amino acid, preferably threonine, for the residue at position 408 in the amino acid sequence of SEQ ID NO: 1;

(15b) a substitution of an uncharged amino acid, preferably leucine, for the residue at position 418 in the amino acid sequence of SEQ ID NO: 1;

(16b) a substitution of an amino acid other than proline, glycine, cysteine, and threonine, preferably aspartic acid, glutamic acid, arginine, histidine, glutamine, asparagine, lysine, alanine, valine, tryptophan, or serine, more preferably alanine, serine, histidine, aspartic acid, or glutamic acid, even more preferably alanine, serine, or histidine, most preferably histidine, for the residue at position 420 in the amino acid sequence of SEQ ID NO: 1;

(17b) a substitution of an uncharged amino acid, preferably threonine, for the residue at position 421 in the amino acid sequence of SEQ ID NO: 1;

(18b) a substitution of a nonpolar amino acid, preferably alanine, for the residue at position 434 in the amino acid sequence of SEQ ID NO: 1; and (19b) a substitution of a nonpolar amino acid, preferably valine, for the residue at position 442 in the amino acid sequence of SEQ ID NO: 1.

In view of further improvement of stereoselectivity, the polypeptide preferably has amino acid substitutions of one or more types selected from the group consisting of the following types (1c) to (13c):

(1c) a substitution of an uncharged amino acid, preferably threonine, for the residue at position 161 and a substitution of an uncharged amino acid, preferably leucine, for the residue at position 418 in the amino acid sequence of SEQ ID NO: 1;

(2c) a substitution of an uncharged amino acid, preferably threonine, for the residue at position 161 and a substitution of an uncharged amino acid, preferably isoleucine, for the residue at position 284 in the amino acid sequence of SEQ ID NO: 1;

(3c) a substitution of an uncharged amino acid, preferably threonine, for the residue at position 161, a substitution of a nonpolar amino acid, preferably isoleucine, for the residue at position 236, and a substitution of a nonpolar amino acid, preferably valine, for the residue at position 442 in the amino acid sequence of SEQ ID NO: 1;

(4c) a substitution of an uncharged amino acid, preferably threonine, for the residue at position 161, a substitution of a nonpolar amino acid, preferably alanine, for the residue at position 209, and a substitution of a nonpolar amino acid, preferably valine, for the residue at position 235 in the amino acid sequence of SEQ ID NO: 1;

(5c) a substitution of an uncharged amino acid, preferably threonine, for the residue at position 161 and a substitution of a nonpolar amino acid, preferably alanine, for the residue at position 434 in the amino acid sequence of SEQ ID NO: 1;

(6c) a substitution of an uncharged amino acid, preferably tyrosine, for the residue at position 42 and a substitution of an uncharged amino acid, preferably threonine, for the residue at position 408 in the amino acid sequence of SEQ ID NO: 1;

(7c) a substitution of a basic amino acid, preferably lysine, for the residue at position 29 and a substitution of a nonpolar amino acid, preferably valine, for the residue at position 262 in the amino acid sequence of SEQ ID NO: 1;

(8c) a substitution of an uncharged amino acid, preferably glycine, for the residue at position 11, a substitution of a basic amino acid, preferably histidine, for the residue at position 151, and a substitution of a nonpolar amino acid, preferably valine, for the residue at position 62 in the amino acid sequence of SEQ ID NO: 1;

(9c) a substitution of an uncharged amino acid, preferably cysteine, for the residue at position 84 and a substitution of an uncharged amino acid other than threonine, preferably serine, for the residue at position 420 in the amino acid sequence of SEQ ID NO: 1;

(10c) a substitution of an uncharged amino acid, preferably threonine, for the residue at position 161 and a substitution of a nonpolar amino acid, preferably isoleucine, for the residue at position 17 in the amino acid sequence of SEQ ID NO: 1;

(11c) a substitution of an uncharged amino acid, preferably threonine, for the residue at position 161 and a substitution of a basic amino acid, preferably histidine, for the residue at position 420 in the amino acid sequence of SEQ ID NO: 1;

(12c) a substitution of a nonpolar amino acid, preferably isoleucine, for the residue at position 17 and a substitution of a basic amino acid, preferably histidine, for the residue at position 420 in the amino acid sequence of SEQ ID NO: 1; and (13c) a substitution of an uncharged amino acid, preferably threonine, for the residue at position 161, a substitution of a nonpolar amino acid, preferably isoleucine, for the residue at position 17, and a substitution of a basic amino acid, preferably histidine, for the residue at position 420 in the amino acid sequence of SEQ ID NO: 1.

(b) Thermal Stability

In view of thermal stability improvement, the polypeptide preferably has one or more substitutions for the amino acid residue or residues at one or more positions selected from positions 3, 17, 116, and 190 in the amino acid sequence of SEQ ID NO: 1 in the Sequence Listing, or preferably has one or more amino acid residues added to one or both of the N- and C-termini of the amino acid sequence having said substitution(s).

More preferably, the polypeptide has one or more amino acid substitutions selected from the group consisting of the following types (1d) to (4d):

(1d) a substitution of a basic amino acid, preferably arginine, for the residue at position 3 in the amino acid sequence of SEQ ID NO: 1;

(2d) a substitution of a nonpolar amino acid, preferably leucine, for the residue at position 17 in the amino acid sequence of SEQ ID NO: 1;

(3d) a substitution of a nonpolar amino acid, preferably leucine, for the residue at position 116 in the amino acid sequence of SEQ ID NO: 1; and (4d) a substitution of a nonpolar amino acid, preferably tyrosine, for the residue at position 190 in the amino acid sequence of SEQ ID NO: 1.

In view of further improvement of thermal stability, the polypeptide preferably has a substitution of preferably a basic amino acid, more preferably arginine, for the residue at position 3, a substitution of a nonpolar amino acid, preferably leucine, for the residue at position 17, and a substitution of a nonpolar amino acid, preferably leucine, for the residue at position 116.

(c) Stability in the Presence of (S)-7-methoxy-2-aminotetralin

In view of improvement of the stability in the presence of (S)-7-methoxy-2-aminotetralin, the polypeptide preferably has one or more substitutions for the amino acid residue or residues at one or more positions selected from positions 3, 11, 17, 29, 42, 84, 116, 151, 153, 161, 171, 176, 284, 190, 209, 235, 236, 262, 302, 408, 418, 420, 434, 435, and 442 in the amino acid sequence of SEQ ID NO: 1 in the Sequence Listing, or preferably has one or more amino acid residues added to one or both of the N- and C-termini of the amino acid sequence having said substitution(s).

More preferably, the polypeptide has one or more amino acid substitutions selected from the group consisting of the following types (1e) to (25e):

(1e) a substitution of a basic amino acid, preferably arginine, for the residue at position 3 in the amino acid sequence of SEQ ID NO: 1;

(2e) a substitution of an uncharged amino acid, preferably glycine, for the residue at position 11 in the amino acid sequence of SEQ ID NO: 1;

(3e) a substitution of a nonpolar amino acid, preferably isoleucine or leucine, for the residue at position 17 in the amino acid sequence of SEQ ID NO: 1;

(4e) a substitution of a basic amino acid, preferably lysine, for the residue at position 29 in the amino acid sequence of SEQ ID NO: 1;

(5e) a substitution of an uncharged amino acid, preferably tyrosine, for the residue at position 42 in the amino acid sequence of SEQ ID NO: 1;

(6e) a substitution of an uncharged amino acid, preferably cysteine, for the residue at position 84 in the amino acid sequence of SEQ ID NO: 1;

(7e) a substitution of a nonpolar amino acid, preferably leucine, for the residue at position 116 in the amino acid sequence of SEQ ID NO: 1;

(8e) a substitution of a basic amino acid, preferably histidine, for the residue at position 151 in the amino acid sequence of SEQ ID NO: 1;

(9e) a substitution of a nonpolar amino acid, preferably phenylalanine, for the residue at position 153 in the amino acid sequence of SEQ ID NO: 1;

(10e) a substitution of an uncharged amino acid or a nonpolar amino acid, preferably threonine or valine, for the residue at position 161 in the amino acid sequence of SEQ ID NO: 1;

(11e) a substitution of a basic amino acid, preferably arginine, for the residue at position 171 in the amino acid sequence of SEQ ID NO: 1;

(12e) a substitution of an uncharged amino acid, preferably serine, for the residue at position 176 in the amino acid sequence of SEQ ID NO: 1;

(13e) a substitution of an uncharged amino acid, preferably isoleucine, for the residue at position 284 in the amino acid sequence of SEQ ID NO: 1;

(14e) a substitution of a nonpolar amino acid, preferably tyrosine, for the residue at position 190 in the amino acid sequence of SEQ ID NO: 1;

(15e) a substitution of a nonpolar amino acid, preferably alanine, for the residue at position 209 in the amino acid sequence of SEQ ID NO: 1;

(16e) a substitution of a nonpolar amino acid, preferably valine, for the residue at position 235 in the amino acid sequence of SEQ ID NO: 1;

(17e) a substitution of a nonpolar amino acid, preferably isoleucine, for the residue at position 236 in the amino acid sequence of SEQ ID NO: 1;

(18e) a substitution of a nonpolar amino acid, preferably valine, for the residue at position 262 in the amino acid sequence of SEQ ID NO: 1;

(19e) a substitution of a nonpolar amino acid, preferably isoleucine, for the residue at position 302 in the amino acid sequence of SEQ ID NO: 1;

(20e) a substitution of an uncharged amino acid, preferably threonine, for the residue at position 408 in the amino acid sequence of SEQ ID NO: 1;

(21e) a substitution of an uncharged amino acid, preferably leucine, for the residue at position 418 in the amino acid sequence of SEQ ID NO: 1;

(22e) a substitution of a nonpolar amino acid or an uncharged amino acid other than threonine, or a basic amino acid, preferably alanine, histidine, or serine, for the residue at position 420 in the amino acid sequence of SEQ ID NO: 1;

(23e) a substitution of an uncharged amino acid, preferably threonine, for the residue at position 421 in the amino acid sequence of SEQ ID NO: 1;

(24e) a substitution of a nonpolar amino acid, preferably alanine, for the residue at position 434 in the amino acid sequence of SEQ ID NO: 1;

(25e) a substitution of a nonpolar amino acid, preferably alanine, for the residue at position 435 in the amino acid sequence of SEQ ID NO: 1; and (26e) a substitution of a nonpolar amino acid, preferably valine, for the residue at position 442 in the amino acid sequence of SEQ ID NO: 1.

In view of further improvement of the stability in the presence of (S)-7-methoxy-2-aminotetralin, the polypeptide preferably has amino acid substitutions of one or more types selected from the group consisting of the following types (1f) to (15f):

(1f) a substitution of an uncharged amino acid, preferably threonine, for the residue at position 161 and a substitution of an uncharged amino acid, preferably leucine, for the residue at position 418 in the amino acid sequence of SEQ ID NO: 1;

(2f) a substitution of an uncharged amino acid, preferably threonine, for the residue at position 161, a substitution of a nonpolar amino acid, preferably isoleucine, for the residue at position 236, and a substitution of a nonpolar amino acid, preferably valine, for the residue at position 442 in the amino acid sequence of SEQ ID NO: 1;

(3f) a substitution of an uncharged amino acid, preferably threonine, for the residue at position 161 and a substitution of a nonpolar amino acid, preferably alanine, for the residue at position 434 in the amino acid sequence of SEQ ID NO: 1;

(4f) a substitution of an uncharged amino acid, preferably glycine, for the residue at position 11, a substitution of a basic amino acid, preferably histidine, for the residue at position 151, a substitution of an uncharged amino acid, preferably threonine, for the residue at position 161, and a substitution of a nonpolar amino acid, preferably valine, for the residue at position 262 in the amino acid sequence of SEQ ID NO: 1;

(5f) a substitution of an uncharged amino acid, preferably threonine, for the residue at position 161, a substitution of a nonpolar amino acid, preferably alanine, for the residue at position 209, and a substitution of a nonpolar amino acid, preferably valine, for the residue at position 235 in the amino acid sequence of SEQ ID NO: 1;

(6f) a substitution of an uncharged amino acid, preferably tyrosine, for the residue at position 42 and a substitution of an uncharged amino acid, preferably threonine, for the residue at position 408 in the amino acid sequence of SEQ ID NO: 1;

(7f) a substitution of a nonpolar amino acid, preferably leucine, for the residue at position 17 and a substitution of a nonpolar amino acid, preferably phenylalanine, for the residue at position 153 in the amino acid sequence of SEQ ID NO: 1;

(8f) a substitution of a basic amino acid, preferably lysine, for the residue at position 29 and a substitution of a nonpolar amino acid, preferably valine, for the residue at position 262 in the amino acid sequence of SEQ ID NO: 1;

(9f) a substitution of an uncharged amino acid, preferably threonine, for the residue at position 161 and a substitution of an uncharged amino acid, preferably isoleucine, for the residue at position 284 in the amino acid sequence of SEQ ID NO: 1;

(10f) a substitution of a basic amino acid, preferably arginine, for the residue at position 3, a substitution of a nonpolar amino acid, preferably leucine, for the residue at position 17, a substitution of a nonpolar amino acid, preferably leucine, for the residue at position 116, and a substitution of a nonpolar amino acid, preferably tyrosine, for the residue at position 190 in the amino acid sequence of SEQ ID NO: 1;

(11f) a substitution of an uncharged amino acid, preferably cysteine, for the residue at position 84 and a substitution of an uncharged amino acid other than threonine, preferably serine, for the residue at position 420 in the amino acid sequence of SEQ ID NO: 1;

(12f) a substitution of an uncharged amino acid, preferably threonine, for the residue at position 161 and a substitution of a nonpolar amino acid, preferably isoleucine, for the residue at position 17 in the amino acid sequence of SEQ ID NO: 1;

(13f) a substitution of an uncharged amino acid, preferably threonine, for the residue at position 161 and a substitution of a basic amino acid, preferably histidine, for the residue at position 420 in the amino acid sequence of SEQ ID NO: 1;

(14f) a substitution of a nonpolar amino acid, preferably leucine, for the residue at position 17 and a substitution of a basic amino acid, preferably histidine, for the residue at position 420 in the amino acid sequence of SEQ ID NO: 1; and (15f) a substitution of an uncharged amino acid, preferably threonine, for the residue at position 161, a substitution of a nonpolar amino acid, preferably isoleucine, for the residue at position 17, and a substitution of a basic amino acid, preferably histidine, for the residue at position 420 in the amino acid sequence of SEQ ID NO: 1.

(d) Activity to 7-methoxy-2-tetralone

In view of improvement of the activity to 7-methoxy-2-tetralone, the polypeptide preferably has one or more substitutions for the amino acid residue or residues at one or more positions selected from positions 17, 84, 420, and 421 of SEQ ID NO: 1 in the Sequence Listing, or preferably has one or more amino acid residues added to one or both of the N- and C-termini of the amino acid sequence having said substitution(s).

Preferably, the polypeptide has an amino acid substitution selected from the group consisting of the following types (1g) to (4g):

(1g) a substitution of a nonpolar amino acid, preferably leucine, for the residue at position 17 in the amino acid sequence of SEQ ID NO: 1;

(2g) a substitution of an uncharged amino acid, preferably cysteine, for the residue at position 84 in the amino acid sequence of SEQ ID NO: 1;

(3g) a substitution of a nonpolar amino acid or an uncharged amino acid other than threonine, preferably alanine or serine, for the residue at position 420 in the amino acid sequence of SEQ ID NO: 1; and (4g) a substitution of an uncharged amino acid, preferably threonine, for the residue at position 421 in the amino acid sequence of SEQ ID NO: 1.

In view of further improvement of the activity to 7-methoxy-2-tetralone, the polypeptide preferably has a substitution of an uncharged amino acid, preferably cysteine, for the residue at position 84 and a substitution of an amino acid other than threonine, preferably serine, for the residue at position 420 in the amino acid sequence of SEQ ID NO: 1.

(e) (S)-7-methoxy-2-aminotetralin-Induced Competitive Inhibition

In view of a reduction in (S)-7-methoxy-2-aminotetralin-induced competitive inhibition, the polypeptide preferably has one or more substitutions for the amino acid residue or residues at one or more positions selected from positions 11, 17, 151, 153, 161, 171, 176, 284, 209, 235, 236, 262, 302, 418, 434, 435, and 442 in the amino acid sequence of SEQ ID NO: 1 in the Sequence Listing, or preferably has one or more amino acid residues added to one or both of the N- and C-termini of the amino acid sequence having said substitution(s).

More preferably, the polypeptide has one or more amino acid substitutions selected from the group consisting of the following types (1h) to (17h):

(1h) a substitution of an uncharged amino acid, preferably glycine, for the residue at position 11 in the amino acid sequence of SEQ ID NO: 1;

(2h) a substitution of a nonpolar amino acid, preferably isoleucine or leucine, for the residue at position 17 in the amino acid sequence of SEQ ID NO: 1;

(3h) a substitution of a basic amino acid, preferably histidine, for the residue at position 151 in the amino acid sequence of SEQ ID NO: 1;

(4h) a substitution of a nonpolar amino acid, preferably phenylalanine, for the residue at position 153 in the amino acid sequence of SEQ ID NO: 1;

(5h) a substitution of an uncharged amino acid or a nonpolar amino acid, preferably threonine or valine, for the residue at position 161 in the amino acid sequence of SEQ ID NO: 1;

(6h) a substitution of a basic amino acid, preferably arginine, for the residue at position 171 in the amino acid sequence of SEQ ID NO: 1;

(7h) a substitution of an uncharged amino acid, preferably serine, for the residue at position 176 in the amino acid sequence of SEQ ID NO: 1;

(8h) a substitution of an uncharged amino acid, preferably isoleucine, for the residue at position 284 in the amino acid sequence of SEQ ID NO: 1;

(9h) a substitution of a nonpolar amino acid, preferably alanine, for the residue at position 209 in the amino acid sequence of SEQ ID NO: 1;

(10h) a substitution of a nonpolar amino acid, preferably valine, for the residue at position 235 in the amino acid sequence of SEQ ID NO: 1;

(11h) a substitution of a nonpolar amino acid, preferably isoleucine, for the residue at position 236 in the amino acid sequence of SEQ ID NO: 1;

(12h) a substitution of a nonpolar amino acid, preferably valine, for the residue at position 262 in the amino acid sequence of SEQ ID NO: 1;

(13h) a substitution of a nonpolar amino acid, preferably isoleucine, for the residue at position 302 in the amino acid sequence of SEQ ID NO: 1;

(14h) a substitution of an uncharged amino acid, preferably leucine, for the residue at position 418 in the amino acid sequence of SEQ ID NO: 1;

(15h) a substitution of a nonpolar amino acid, preferably alanine, for the residue at position 434 in the amino acid sequence of SEQ ID NO: 1;

(16h) a substitution of a nonpolar amino acid, preferably alanine, for the residue at position 435 in the amino acid sequence of SEQ ID NO: 1; and (17h) a substitution of a nonpolar amino acid, preferably valine, for the residue at position 442 in the amino acid sequence of SEQ ID NO: 1.

In view of further enhancement of the effect of reducing (S)-7-methoxy-2-aminotetralin-induced competitive inhibition, the polypeptide preferably has amino acid substitutions of at least one type selected from the group consisting of the following types:

(1i) a substitution of an uncharged amino acid, preferably threonine, for the residue at position 161 and a substitution of an uncharged amino acid, preferably leucine, for the residue at position 418 in the amino acid sequence of SEQ ID NO: 1;

(2i) a substitution of an uncharged amino acid, preferably threonine, for the residue at position 161, a substitution of a nonpolar amino acid, preferably isoleucine, for the residue at position 236, and a substitution of a nonpolar amino acid, preferably valine, for the residue at position 442 in the amino acid sequence of SEQ ID NO: 1;

(3i) a substitution of an uncharged amino acid, preferably threonine, for the residue at position 161 and a substitution of a nonpolar amino acid, preferably alanine, for the residue at position 434 in the amino acid sequence of SEQ ID NO: 1;

(4i) a substitution of an uncharged amino acid, preferably glycine, for the residue at position 11, a substitution of a basic amino acid, preferably histidine, for the residue at position 151, a substitution of an uncharged amino acid, preferably threonine, for the residue at position 161, and a substitution of a nonpolar amino acid, preferably valine, for the residue at position 262 in the amino acid sequence of SEQ ID NO: 1;

(5i) a substitution of an uncharged amino acid, preferably threonine, for the residue at position 161, a substitution of a nonpolar amino acid, preferably alanine, for the residue at position 209, and a substitution of a nonpolar amino acid, preferably phenylalanine, for the residue at position 153 in the amino acid sequence of SEQ ID NO: 1;

(6i) a substitution of a nonpolar amino acid, preferably leucine, for the residue at position 17 and a substitution of a nonpolar amino acid, preferably phenylalanine, for the residue at position 153 in the amino acid sequence of SEQ ID NO: 1; and (7i) a substitution of an uncharged amino acid, preferably threonine, for the residue at position 161 and a substitution of an uncharged amino acid, preferably isoleucine, for the residue at position 284 in the amino acid sequence of SEQ ID NO: 1.

According to the description, for example, the ability to catalyze a reaction to produce (S)-7-methoxy-2-aminotetralin from 7-methoxy-2-tetralone in the presence of an amino group donor can be determined as described below.

Specifically, 100 μL of a cell-free extract containing the enzyme is added to 305 μL of a substrate solution having the composition shown below. After the mixture is allowed to react at 30° C. for 1 hour, 50 μL of 6 N hydrochloric acid is added to stop the reaction. The optical purity of the produced (S)-7-methoxy-2-aminotetralin is measured using high-performance liquid chromatography. In this case, the activity of production of (S)-7-methoxy-2-aminotetralin per 1 mg of the enzyme is preferably at least 1 mU/mg, more preferably at least 10 mU/mg, even more preferably at least 100 mU/mg. The optical purity of the produced (S)-7-methoxy-2-aminotetralin is preferably at least 80% ee, more preferably at least 90% ee, even more preferably at least 95% ee.

[The Composition of the Substrate Solution]

| | |
|---|---|
| (S)-1-phenethylamine | 21 mM |
| Potassium phosphate (pH 7.5) | 0.1M |
| 7-methoxy-2-tetralone | 14 mM |

[Measurement Conditions for High-Performance Liquid Chromatography]

Column: Crownpak CR (+) (manufactured by Daicel Corporation)
Eluent: aqueous perchloric acid solution (pH 1.5)/methanol=85/15 (volume ratio)
Flow rate: 1 mL/minute
Detection: 220 nm
Column temperature: 47° C.

(a) High Stereoselectivity for 7-methoxy-2-tetralone

As used herein, the term "stereoselectivity" means the optical purity of an amino compound produced from a ketone compound as a substrate. The stereoselectivity also means the selectivity obtained when in the presence of a ketone compound, the amino group of one enantiomer of racemic amino compounds is transferred to the ketone compound.

For example, the stereoselectivity can be determined as described below.

(a)-1

A hundred μL of a cell-free extract containing the enzyme is added to 305 μL of a substrate solution having the composition shown below. After the mixture is allowed to react at 30° C. for 1 hour, 50 μL of 6 N hydrochloric acid is added to stop the reaction. The optical purity of the produced (S)-7-methoxy-2-aminotetralin is measured using high-performance liquid chromatography.

[The Composition of the Substrate Solution]

| (S)-1-phenethylamine | 21 mM |
|---|---|
| Potassium phosphate (pH 7.5) | 0.1M |
| 7-methoxy-2-tetralone | 14 mM |

[Measurement Conditions for High-Performance Liquid Chromatography]

Column: Crownpak CR (+) (manufactured by Daicel Corporation)
Eluent: aqueous perchloric acid solution (pH 1.5)/methanol=85/15 (volume ratio)
Flow rate: 1 mL/minute
Detection: 220 nm
Column temperature: 47° C.

(a)-2

The stereoselectivity can also be determined as described below.

Genes of the aminotransferase of interest, L-lactic acid dehydrogenase derived from *Pediococcus acidilactici* strain JCM8797 (PALDH) described in WO 2007/139255, and glucose dehydrogenase (GHD) derived from *Bacillus megaterium* strain IAM1030 are inserted into plasmid vectors, respectively or into the same plasmid vector. *Escherichia coli* (*E. coli*) or the like is transformed with the vector or vectors, and the enzymes are expressed in the *E. coli*. The three enzymes may be expressed in a single species of *E. coli* or two or three species of *E. coli*, respectively. Cells of each bacterium are subjected to sonication or the like so that a cell-free extract is obtained. Among the three enzymes, PALDH and GDH are added in excess with respect to the activity of the aminotransferase. Subsequently, 250 μL of a substrate solution having the composition shown below is added to 250 μL of the enzyme mixture. After the resulting mixture is allowed to react at 35° C. for 1.5 hours, 50 μL of 6 N hydrochloric acid is added to stop the reaction. The optical purity of the produced (S)-7-methoxy-2-aminotetralin is measured using the high-performance liquid chromatography.

[The Composition of the Substrate Solution]

| Potassium phosphate (pH 6.8) | 0.2M |
|---|---|
| L-alanine | 1.12M |
| D-glucose | 340 mM |
| NADH | 0.2 mM |
| Pyridoxal phosphate | 0.8 mM |
| 7-methoxy-2-tetralone | 228 mM |

In the description, modified aminotransferase with higher stereoselectivity means that when the above reaction is performed using it, the optical purity of the produced (S)-7-methoxy-2-aminotetralin is at least 0.1% e.e., preferably at least 0.5% e.e., more preferably at least 1.0% e.e. higher than that produced using the wild-type in at least one of the reactions (a)-1 and (a)-2. In a preferred mode, it means that in the reaction (a)-2, the optical purity is at least 0.1% e.e., preferably at least 0.5% e.e., more preferably at least 1.0% e.e. higher than that produced using the wild-type.

(b) High Thermal Stability

For example, the thermal stability of the enzyme can be determined as described below.

Recombinant *E. coli* capable of expressing the aminotransferase of interest is inoculated into 5 mL of a 2×YT medium containing 200 μg/mL of ampicillin and cultured with shaking at 30° C. overnight. The bacterial cells are obtained by centrifugation of 1 mL of the resulting culture. To the bacterial cells is added 1 mL of a 0.1 M potassium phosphate buffer (pH 7.0) containing 0.5 mM of pyridoxal phosphate, and the mixture is sonicated so that a cell-free extraction is obtained. After 500 μL of the cell-free extract is incubated at 75° C. for 30 minutes, the extract is cooled to 4° C. The cell-free extract is diluted with a 0.1 M potassium phosphate buffer (pH 7.5) containing 0.5 mM of pyridoxal phosphate. After 100 μL of the diluted cell-free extract is added to 305 μL of a substrate solution having the composition shown below, the mixture is allowed to react at 30° C. for 1 hour. Subsequently, 50 μL of 6 N hydrochloric acid is added to stop the reaction. The optical purity of the produced (S)-7-methoxy-2-aminotetralin is measured using high-performance liquid chromatography. The remaining activity is determined by comparison with a sample not undergoing the heat treatment.

[The Composition of the Substrate Solution]

| (S)-1-phenethylamine | 21 mM |
|---|---|
| Potassium phosphate (pH 7.5) | 0.1M |
| 7-methoxy-2-tetralone | 14 mM |

[Measurement Conditions for High-Performance Liquid Chromatography]

Column: Cosmosil 5C8-MS (manufactured by NACALAI TESQUE, INC.)
Eluent: 30 mM potassium phosphate buffer (pH 2.5)/acetonitrile/methanol=4/1/1 (volume ratio)
Flow rate: 0.9 mL/minute
Detection: 254 nm In the description, modified aminotransferase with higher thermal stability means that when the above evaluation is performed, the remaining activity of it is at least 1%, preferably at least 5%, more preferably at least 10%, most preferably at least 20% higher than that of the wild-type.

(c) High Stability in the Presence of (S)-7-methoxy-2-aminotetralin

For example, the stability of the enzyme in the presence of a product, (S)-7-methoxy-2-aminotetralin, can be determined as described below.

(c)-1

To 100 µL of a cell-free extract containing the enzyme is added 900 µL of a 0.1 M potassium phosphate buffer (pH 6.3) containing 1% of 7-methoxy-2-aminotetralin hydrochloride, and the mixture is incubated at 35° C. or 45° C. The mixture is sampled in an amount of 100 µL at reaction times 0 and 20 hours, respectively, and each sample is diluted 200 times with an aqueous 0.1 M potassium phosphate solution (pH 7.5). Subsequently, 200 µL of each dilution is added to 800 µL of a substrate solution having the composition shown below. After the mixture is allowed to react at 30° C. for 1 hour, 50 µL of 6 N hydrochloric acid is added to stop the reaction. The concentration of the produced acetophenone is measured using the high-performance liquid chromatography shown below. The remaining activity at reaction time 20 hours is determined relative to the activity at reaction time 0, which is normalized as 100%.

[The Composition of the Substrate Solution]

| | |
|---|---|
| (S)-1-phenethylamine | 25 mM |
| Sodium pyruvate | 25 mM |
| Pyridoxal phosphate | 2.5 mM |
| Tris (pH 8.5) | 0.1M |

[Measurement Conditions for High-Performance Liquid Chromatography]

Column: Cosmosil 5C8-MS (manufactured by NACALAI TESQUE, INC.)

Eluent: 30 mM potassium phosphate buffer (pH 2.5)/acetonitrile/methanol=4/1/1 (volume ratio)

Flow rate: 0.9 mL/minute

Detection: 254 nm (c)-2

For example, the stability of the enzyme in the presence of (S)-7-methoxy-2-aminotetralin can also be determined as described below.

After 5 mL of a liquid culture was centrifuged to give bacterial cells, 1 mL of a 100 mM potassium phosphate buffer (pH 7.5) containing 0.5 mM of pyridoxal phosphate is added to the bacterial cells. The mixture is sonicated so that a cell-free extraction is obtained.

To a test tube are added 50 µL of the cell-free extract, 600 µL of an aqueous solution (pH 7.5) of 10% or 1.67% (S)-7-methoxy-2-aminotetralin hydrochloride, 100 µL of an aqueous 0.46 M sodium pyruvate solution (pH 7.5), 50 µL of a 1 M MOPS buffer (pH 7.5), 10 µL of an aqueous 50 mM PLP solution (pH 7.5), and 190 µL of water. After argon gas is injected, the tube is hermetically sealed, and the mixture is agitated with a stirrer at 30° C. for 4 hours. The mixture is sampled in an amount of 200 µL, and 50 µL of 0.6 N hydrochloric acid is added to the sample to stop the reaction. The concentration of the produced 7-methoxy-2-tetralone is measured by the method described below using high-performance liquid chromatography. The activity in the case of using an aqueous solution of 1.67% (S)-7-methoxy-2-aminotetralin is normalized as 100%, and then the relative activity in the case of using the aqueous 10% solution is determined.

[Measurement Conditions for High-Performance Liquid Chromatography]

Column: Cosmosil 5C8-MS (manufactured by NACALAI TESQUE, INC.)

Eluent: 30 mM potassium phosphate buffer (pH 2.5)/acetonitrile/methanol=4/1/1 (volume ratio)

Flow rate: 0.9 mL/minute

Detection: 254 nm

In the description, modified aminotransferase with higher stability in the presence of (S)-7-methoxy-2-aminotetralin means that when the above evaluation is performed, the remaining activity of it is at least 1%, preferably at least 5%, more preferably at least 10%, most preferably at least 20% higher than that of the wild-type, after at least one of the reactions (c)-1 and (c)-2. In a preferred mode, it means that the remaining activity is at least 1%, preferably at least 5%, more preferably at least 10%, most preferably at least 20% higher than that of the wild-type after the reaction (c)-1. In a more preferred mode, it means that when the incubation is performed at 45° C. in the reaction (c)-1, the remaining activity is at least 1%, preferably at least 5%, more preferably at least 10%, most preferably at least 20% higher than that of the wild-type.

(d) High Activity to 7-methoxy-2-tetralone

The activity to 7-methoxy-2-tetralone can be determined as described below.

The DNA of the aminotransferase to be evaluated is incorporated into a high-expression vector pUCNT (WO 94/03613), and *E. Coli* HB101 is transformed with this plasmid. The transformed *E. coli* is purified, then inoculated into 5 mL of a 2×YT medium containing 200 µg/mL of ampicillin, and cultured with shaking at 30° C. for 28 hours. The resulting liquid culture is sonicated so that a cell-free extract is obtained. To a test tube are added 50 µL of the cell-free extract, 150 µL of a 0.1 M potassium phosphate buffer (pH 7.5) containing 1 mM of pyridoxal phosphate, 200 µL of a 0.1 M potassium phosphate buffer (pH 7.5) containing 42 mM of (S)-1-phenethylamine, and 5 µL of a DMSO solution containing 20% of 7-methoxy-2-tetralone. After argon gas is injected, the tube is hermetically sealed, and the mixture is agitated with a stirrer at 30° C. for 1 hour. Subsequently, 50 µL of 6 N hydrochloric acid is added to stop the reaction, and the concentration of the produced (S)-7-methoxy-2-aminotetralin is measured using the high-performance liquid chromatography shown below, when the activity is determined.

[Measurement Conditions for High-Performance Liquid Chromatography]

Column: Cosmosil 5C8-MS (manufactured by NACALAI TESQUE, INC.)

Eluent: 30 mM potassium phosphate buffer (pH 2.5)/acetonitrile/methanol=4/1/1 (volume ratio)

Flow rate: 0.9 mL/minute

Detection: 254 nm

In the description, modified aminotransferase with higher activity to 7-methoxy-2-tetralone means that when the above evaluation is performed, the relative activity of it is at least 101%, preferably at least 105%, more preferably at least 110%, most preferably at least 120% when the activity of the wild-type is normalized as 100%.

(e) Reduction in (S)-7-methoxy-2-aminotetralin-Induced Competitive Inhibition (S)-7-methoxy-2-aminotetralin-induced competitive inhibition can be determined as described below.

After 5 mL of a liquid culture is centrifuged to give bacterial cells, 1 mL of a 100 mM potassium phosphate buffer (pH 7.5) containing 0.5 mM of pyridoxal phosphate is added to the bacterial cells. The mixture is sonicated so that a cell-free extract is obtained. To a test tube are added 100 µL of the cell-free extract, 600 µL of an aqueous solution of 10% (S)-7-methoxy-2-aminotetralin hydrochloride, 100 µL of an aqueous 1.13 M (S)-1-phenethylamine solution (pH 7.5), 50 µL of a 1 M MOPS buffer (pH 7.5), 10 µL of an aqueous 50 mM PLP solution (pH 7.5), 10 mg of 7-methoxy-2-tetralone, and 130 µL of water. After argon gas is injected, the tube is hermetically sealed, and the mixture is agitated with a stirrer at 30° C. for 1 hour. The mixture is sampled in an amount of 200 µL, and 50 µL of 0.6 N hydrochloric acid is added to the sample to stop the reaction. The concentration of the produced acetophenone is measured using the high-performance liquid chromatography shown below, when the activity is determined.

[Measurement Conditions for High-Performance Liquid Chromatography]

Column: Cosmosil 5C8-MS (manufactured by NACALAI TESQUE, INC.)

Eluent: 30 mM potassium phosphate buffer (pH 2.5)/acetonitrile/methanol=4/1/1 (volume ratio)

Flow rate: 0.9 mL/minute

Detection: 254 nm

In the description, modified aminotransferase of which (S)-7-methoxy-2-aminotetralin-induced competitive inhibition is reduced means that when the above evaluation is performed, the remaining activity of it is at least 1%, preferably at least 5%, more preferably at least 10%, most preferably at least 20% higher than that of the wild-type.

2. Construction of Random Mutagenesis Library and Assay

Methods for searching for the modified aminotransferase of the invention will be described.

(Preparation of Library)

First, randomly mutated MTA genes are obtained. Using error pone PCR (Leung et al., Technique 1, 11-15, 1989) or a kit based on the same principle, such as Diversify PCR Random Mutagenesis Kit (manufactured by Clontech Laboratories, Inc.), DNA fragments can be obtained from the full length of the MTA gene (WO 2006/126498) derived from *Pseudomonas fluorescens* strain KNK08-18 by random introduction of substitution, insertion, and/or deletion of one or more base sequences into the gene. The amplified fragments are incorporated into a suitable vector, such as a high-expression vector pUCNT (WO 94/03613), and *E. coli* HB101 is transformed with the plasmid. The transformed *E. coli* is applied to an LB plate medium containing 100 µg/mL of ampicillin, and a single colony of the *E. coli* is obtained. An enzyme mutant library having additional mutations may also be prepared by the same process using the mutated enzyme gene, which is obtained by the above process, in place of the wild-type gene. The modified aminotransferase of the invention can be selected from the library. The method for the selection is preferably, but not particularly limited to, the method described below.

(Method for Selecting Enzyme with Higher Stability to Product by Plate Evaluation)

Each recombinant *E. coli* in the enzyme mutant library is applied to an LB plate medium containing 100 µg/mL of ampicillin and incubated at 30° C. overnight, and the bacterial cells are obtained. The resulting bacterial cells are inoculated on an LB plate medium containing 4% of 7-methoxy-2-aminotetralin hydrochloride and incubated at 37° C. overnight. The wild-type does not change in color because the enzyme is inhibited or deactivated by a high concentration of (S)-7-methoxy-2-aminotetralin, but mutants retaining the activity changes into black by producing 7-methoxy-2-aminotetralone, which is an unstable compound. The DNA sequence from the colored strain is examined so that any modified amino acid sequence can be identified.

(Cell-Free Assay)

Each recombinant *E. coli* in the enzyme mutant library is inoculated into 5 mL of a 2× YT medium (tryptone 1.6%, yeast extract 1.0%, sodium chloride 0.5%, pH 7.0) containing 200 µg/mL of ampicillin and cultured with shaking at 30° C. for 28 hours. To 500 µL of the resulting liquid culture is added 500 µL of a 0.2 M potassium phosphate buffer (pH 7.5) containing 1 mM of pyridoxal phosphate, and the mixture is sonicated so that a cell-free extract is obtained. The above stereoselectivity and the above stability to (S)-7-methoxy-2-aminotetralin are examined using the cell-free extract solution, so that modified aminotransferases having properties better than those of the wild-type can be selected.

3. Production of Multiply-Mutated Enzymes and Saturation Mutagenesis

The mutated site of the resulting modified aminotransferase may be changed to any other amino acid residue(s) by site-directed mutagenesis, so that a modified enzyme having far better properties can be obtained. Some mutations in one or both of the resulting different modified aminotransferases may be combined using site-directed mutagenesis, so that a modified aminotransferase having enhanced properties of one type or having properties of both types can be produced. The enzyme of the invention is intended to include such enzymes.

(Method (1) for Preparing Mutated Enzymes)

Examples of the site-directed mutagenesis include the methods described in Olfert Landt et al., Gene, 96, 125-128, 1990, Smith et al., Genetic Engineering, 3 1 Setlow, J. and Hollaender, A Plenum, New York, Vlasuk et al., Experimental Manipulation of Gene Expression, Inouye, M., Academic Press, New York, and Hos.N. Hunt et al., Gene, 77, 51, 1989, and methods using a commercially available kit, such as QuikChange II Kit (manufactured by Stratagene). To introduce mutations into two or more sites, a method according to the above may be repeated, so that DNA encoding the desired polypeptide of the invention can be obtained.

4. DNA of the Invention

The DNA of the invention is polypeptide-encoding DNA obtained by the process described above, which may be of any type capable of expressing the polypeptide in a host cell when introduced by the method described below into the host cell, and may contain any untranslated region. For example, the DNA of the invention is preferably a DNA that encodes a polypeptide having at least 85% sequence identity to the amino acid sequence of SEQ ID NO: 1, having the ability to produce (S)-7-methoxy-2-aminotetralin from 7-methoxy-2-tetralone in the presence of an amino group donor, and having reactivity higher than that of the wild-type enzyme, and hybridizes under stringent conditions with DNA having a base sequence complementary to DNA consisting of the base sequence of SEQ ID NO: 2 in the Sequence Listing.

As used herein, the term "DNA that hybridizes under stringent conditions with DNA having a base sequence complementary to DNA consisting of the base sequence of SEQ ID NO: 2 in the Sequence Listing" means DNA that can be obtained by colony hybridization, plaque hybridization, Southern hybridization, or other techniques under stringent conditions using, as a probe, DNA consisting of a base sequence complementary to the base sequence of SEQ ID NO: 2 in the Sequence Listing.

Hybridization can be performed according to the methods described in Molecular Cloning, A Laboratory Manual, second edition (Cold Spring Harbor Laboratory Press, 1989) or other publications. As used herein, DNA that hybridizes under stringent conditions may be, for example, DNA that can be obtained by a process including performing hybridization at 65° C. in the presence of 0.7-1.0 M NaCl using a filter on which colony- or plaque-derived DNA is fixed, and then washing the filter with a 2×SSC solution (the composition of a 1×SSC solution: 150 mM sodium chloride and 15 mM sodium citrate) under conditions at 65° C. The DNA is preferably obtained after the filter is washed at 65° C. with a 1×SSC solution, more preferably with a 0.5×SSC solution, even more preferably with a 0.2×, 0.1×, or 0.05×SSC solution.

DNA hybridizable under the above conditions is preferably DNA having at least 74%, more preferably at least 78%, even more preferably at least 85%, 90%, or 94% sequence identity to the DNA represented by SEQ ID NO: 2 in the Sequence Listing, and any DNA is encompassed by such DNA as long as the polypeptide encoded by it has the above transamination activity.

The DNA of the invention is also easily available to those skilled in the art through chemical synthesis or other processes.

5. Vector

A vector DNA may be used to introduce the DNA according to an embodiment of the invention into a host microorganism and to express the DNA. Such a vector DNA may be of any type capable of expressing the gene encoded by the DNA in a suitable host microorganism. Examples of such a vector DNA include plasmid vectors, phage vectors, cosmid vectors, etc. A shuttle vector that makes possible genetic exchange between different host strains may also be used.

Such a vector preferably includes a regulator such as an operably linked promoter (e.g., lacUV5 promoter, trp promoter, trc promoter, tac promoter, lpp promoter, tufB promoter, recA promoter, pL promoter) and an expression unit operably linked to the DNA of the invention. Examples thereof include pUC18 (manufactured by Toyobo Co., Ltd.), pUC19 (manufactured by Toyobo Co., Ltd.), and pUCNT (WO 94/03613 A).

The term "regulator" refers to a base sequence including a functional promoter and any optional related transcription element (such as an enhancer, a CCAAT box, a TATA box, or an SPI site).

The term "operably linked" means that the gene and various regulatory elements, such as a promoter and an enhancer, which regulate the expression of the gene, are linked together so that they can work in a host cell. It is well known to those skilled in the art that the type and kind of the regulator may vary with the host.

Vectors, promoters, and other elements that can be used in a variety of organisms are described in detail in publications such as Biseibutsugaku Kiso Koza, 8, Idensikogaku, Kyoritsu Shuppan, 1987 (in Japanese).

6. Host and Transformant

A host organism may be used to express the DNA according to an embodiment of the invention. Such a host organism may be of any type capable of being transformed with an expression vector containing DNA encoding each polypeptide and capable of expressing the polypeptide from the introduced DNA. Examples of available microorganisms include bacteria for which host-vector systems have been developed, such as *Escherichia, Bacillus, Pseudomonas, Serratia, Brevibacterium, Corynebacterium, Streptococcus,* and *Lactobacillus*; actinomycetes for which host-vector systems have been developed, such as *Rhodococcus* and *Streptomyces*; yeasts for which host-vector systems have been developed, such as *Saccharomyces, Kluyveromyces, Schizosaccharomyces, Zygosaccharomyces, Yarrowia, Trichosporon, Rhodosporidium, Pichia,* and *Candida*; and fungi for which host-vector systems have been developed, such as *Neurospora, Aspergillus, Cephalosporium,* and *Trichoderma*. Besides microorganisms, a variety of host-vector systems have been developed for plants and animals, and especially, systems capable of expressing a large amount of a foreign protein in an insect such as a silkworm (Nature 315, 592-594 (1985)) or a plant such as a rape, a maize, or a potato have been developed, which can be advantageously used. Among them, bacteria are preferred in view of introduction and expression efficiency, and *E. coli* is particularly preferred.

The expression vector containing the DNA of the invention can be introduced into a host microorganism by known methods. For example, *E. coli* may be used as a host microorganism, and in this case, the vector can be introduced into the host cell using commercially available *E. coli* HB101 competent cells (manufactured by TAKARA BIO INC.).

7. Methods for Producing Optically Active Amino Compound

Next, a description will be given of methods for producing an optically active amino compound using the polypeptide according to an embodiment of the invention or using a microorganism having the ability to produce the polypeptide.

The microorganism having the ability to produce the polypeptide according to an embodiment of the invention is typically, but not limited to, a transformant in which a vector containing the DNA according to an embodiment of the invention is incorporated.

The method of the invention for producing an optically active amino compound may be a method including transferring an amino group from an amino group donor to a ketone compound having the same skeleton as the desired amino compound and collecting the produced optically active amino compound (hereinafter referred to as the "production method I"); or a method including selectively transferring an amino group from one enantiomer of an enantiomeric mixture of amino compounds to an amino group acceptor and collecting the remaining enantiomer (optically active amino compound) (hereinafter referred to as the "production method II").

First, the production method I will be described.

(Production Method I)

The production method I includes allowing a ketone compound to react, in the presence of an amino group donor, with the polypeptide of the invention or a culture of a transformant having the ability to produce the polypeptide, so that an optically active amino compound is produced.

This production method typically includes allowing a ketone compound represented by the general formula (1):

to react, in the presence of an amino group donor, with the polypeptide of the invention or a culture of a microorganism having the ability to produce the polypeptide, so that an optically active amino compound represented by the general formula (2):

is produced.

In the formulae (1) and (2), $R^1$ and $R^2$ each represent an optionally substituted alkyl group, an optionally substituted aralkyl group, or an optionally substituted aryl group, and $R^1$ and $R^2$ may be linked together to form a ring. In the formulae, $R^1$ and $R^2$ have different structures.

$R^1$ and $R^2$ are each preferably an optionally substituted alkyl group of 1 to 20 carbon atoms, an optionally substituted aralkyl group of 1 to 20 carbon atoms, or an optionally substituted aryl group of 2 to 20 carbon atoms, more preferably an optionally substituted alkyl group of 1 to 10 carbon atoms, an optionally substituted aralkyl group of 3 to 12 carbon atoms, or an optionally substituted aryl group of 4 to 10 carbon atoms.

The aryl group may be a phenyl group, a naphthyl group, a pyridyl group, a thienyl, an oxadiazolyl group, an imidazolyl group, a thiazolyl group, a furyl group, a pyrrolyl group, a phenoxy group, a naphthoxy group, a pyridyloxy group, a thienyloxy group, an oxadiazolyloxy group, an imidazolyloxy group, a thiazolyloxy group, a furyloxy group, pyrrolyloxy group, or the like.

The alkyl group may be a methyl group, an ethyl group, a propyl group, a butyl group, a pentyl group, a hexyl group, an isopropyl group, a sec-butyl group, a tert-butyl group, a methoxy group, an ethoxy group, a tert-butoxy group, a methoxycarbonyl group, an ethoxycarbonyl group, a tert-butoxycarbonyl group, a vinyl group, an allyl group, a cyclopentyl group, a cyclohexyl group, a cycloheptyl group, or the like. The aralkyl group may be a benzyl group or the like.

These groups may be further substituted, and the substituent may be a halogen atom, a nitrogen atom, a sulfur atom, a hydroxyl group, a nitro group, a cyano group, a methoxy group, an ethoxy group, a carboxyl group, a carboxymethyl group, a carboxyethyl group, a methylenedioxy group, or the like. The ring may be formed through a substituent.

Examples of the ketone compound include 1-tetralone, 2-tetralone, 5-methoxy-2-tetralone, 6-methoxy-2-tetralone, 7-methoxy-2-tetralone, 8-methoxy-2-tetralone, 1-benzyl-3-pyrrolidinone, 1-Boc-3-pyrrolidinone, 1-Cbz-3-pyrrolidinone, 1-benzyl-3-piperidinone, 1-Boc-3-piperidinone, 1-Cbz-3-piperidinone, acetophenone, 3,4-dimethoxyphenylacetone, etc.

(Amino Group Donor)

The amino group donor may be any amino compound capable of reacting with the polypeptide of the invention. Examples of the amino group donor include 1-phenethylamine, 2-butylamine, 2-pentylamine, 2-heptylamine, 3-heptylamine, n-ethylamine, n-propylamine, n-butylamine, n-amylamine, isopropylamine, isobutylamine, glycine, alanine, 3-amino-1-phenylbutane, benzylamine, β-phenethylamine, cyclohexylamine, and optically active compounds thereof. In particular, 1-phenethylamine and alanine are preferred.

(Form of the Polypeptide)

In the production method I, the ketone compound is allowed to react, in the presence of an amino group donor, with the polypeptide of the invention or a culture of a microorganism having the ability to produce the polypeptide.

As used herein, the term "culture" is intended to include a liquid culture containing bacterial cells, cultured bacterial cells, or a processed product therefrom. As used herein, the term "processed product therefrom" typically means a cell-free extract, lyophilized bacterial cells, acetone-dried bacterial cells, or a triturated product of the bacterial cells. The polypeptide and the culture may be used in the form of an immobilized enzyme or immobilized bacterial cells. The immobilization may be achieved by methods well known to those skilled in the art (such as crosslinking methods, physical adsorption methods, or encapsulation methods).

(Improvement of Reactivity by Overcoming Equilibrium in Reaction or Product-Induced Inhibition)

In general, amination based on transamination is a reversible reaction and therefore apparently stops at the equilibrium point. A known method for overcoming the equilibrium in the reaction may be used in combination with the method of the invention so that the reaction with the polypeptide of the invention can be improved. As described in WO 2007/139055, for example, alanine may be used as an amino group donor, and pyruvic acid as a by-product may be converted into lactic acid using lactic acid dehydrogenase in combination with glucose dehydrogenase for coenzyme regeneration, which is an effective method for overcoming the equilibrium in the reaction. Also effective are methods including using alanine as an amino group donor and removing pyruvic acid as a by-product using pyruvate decarboxylase (WO 2007/093372 A1), using alanine dehydrogenase (US 2009/0117627 A1, Evonik Degussa GmbH), using hydrogen peroxide (US 2008/0213845 A1), or using acetobutyric acid synthase (Biosci. Biotechnol. Biochem. 72 (11), 3030-3033 (2008)).

(Substrate Concentration)

Concerning the concentration of the substrate used in the reaction, the concentration of the ketone compound in the liquid composition for the reaction may be 0.1 to 80% by weight, preferably 1 to 50% by weight, and the concentration of the amino group donor may be 80 to 1,200% by mole, preferably 100 to 600% by mole, based on the amount of the ketone compound, when the amino group donor is a chiral amine. When racemic amino compounds are used for the amino group donor, one enantiomer may be used at the above concentration.

(Reaction pH)

The lower limit of the optimum pH range for the polypeptide of the invention is preferably at least pH 4.0, more preferably at least pH 5.0. The upper limit thereof is preferably at most pH 10.0, more preferably at most pH 9.0.

When different polypeptides are used in combination, it is preferred to select pH at which all polypeptides used can work stably at high activity levels.

(Reaction Temperature)

In view of optimal temperature and thermal stability, the temperature of the reaction of the polypeptide of the invention is preferably at least 25° C., more preferably at least 30° C., even more preferably at least 35° C., at least 40° C., or at least 45° C., and preferably at most 80° C., more preferably at most 70° C., even more preferably at most 60° C.

When different polypeptides are used in combination, it is preferred to select a reaction temperature at which all polypeptides used can work stably at high activity levels.

(Solvent)

An aqueous medium such as ion exchanged water or a buffer is usually used as the reaction solvent. Alternatively, the reaction may be performed in the reaction solvent containing an organic solvent. Examples of organic solvents that may be used as needed include alcohol solvents such as methanol, ethanol, 1-propanol, 2-propanol, and 1-butanol; aliphatic hydrocarbon solvents such as pentane and hexane; aromatic hydrocarbon solvents such as benzene and toluene; halogenated hydrocarbon solvents such as methylene chloride and chloroform; ether solvents such as diethyl ether and diisopropyl ether; ester solvents such as ethyl acetate and butyl acetate; ketone solvents such as acetone and methyl ethyl ketone; and others such as acetonitrile.

(Two-Phase System)

If necessary, the organic solvent may be added at a concentration higher than its solubility in water, and the reaction may be performed in the resulting two-phase system. When the organic solvent coexists in the reaction solvent, selectivity, conversion rate, or yield can often increase.

(Reaction Time)

The reaction is generally performed for 1 hour to 1 week, preferably 1 to 72 hours, and the reaction conditions are preferably selected so that the reaction can be completed in such a time.

(Extraction and Purification)

The reaction produces an optically active amino compound. The produced optically active amino compound can be isolated using known methods such as extraction from the liquid reaction mixture, distillation, recrystallization, and column separation.

For example, after the pH is adjusted to be acidic, the unreacted substrate and the ketone compound resulting from the transamination, which corresponds to the amino group donor, may be selectively removed using a common solvent such as an ether such as diethyl ether or diisopropyl ether, an ester such as ethyl acetate or butyl acetate, a hydrocarbon such as hexane, octane, or benzene, or a halogenated hydrocarbon such as methylene chloride, while the produced optically active amino compound is left in the aqueous phase.

For example, the produced optically active amino compound and the unreacted amino group donor can be extracted with a common organic solvent in a similar manner after the pH is adjusted to be basic. For example, the produced optically active amino compound and the unreacted amino group donor can be separated by distillation.

(Production Method II)

Next, the production method II of the invention will be described.

This production method is a method for producing an optically active amino compound by allowing an enantiomeric mixture of amino compounds to react, in the presence of an amino group acceptor, with the polypeptide of the invention or a culture of a transformant having the ability to produce the polypeptide.

For example, this production method includes allowing an enantiomeric mixture of amino compounds represented by the general formula (3):

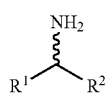

(3)

to react, in the presence of an amino group acceptor, with the polypeptide of the invention or a culture of a microorganism having the ability to produce the polypeptide, so that an optically active amino compound represented by the general formula (4):

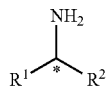

(4)

can be obtained.

In the formulae (3) and (4), $R^1$ and $R^2$ have the same meanings as in the formulae (1) and (2).

Examples of the optically active amino compound include 1-aminotetralin, 2-aminotetralin, 5-methoxy-2-aminotetralin, 6-methoxy-2-aminotetralin, 7-methoxy-2-aminotetralin, 8-methoxy-2-aminotetralin, 1-benzyl-3-aminopyrrolidine, 1-Boc-3-aminopyrrolidine, 1-Cbz-3-aminopyrrolidine, 1-benzyl-3-aminopiperidine, 1-Boc-3-aminopiperidine, 1-Cbz-3-aminopiperidine, 1-phenethylamine, 3,4-dimethoxyamphetamine, etc.

(Amino Group Acceptor)

In this method, a ketone compound is used as an amino group acceptor.

The ketone compound is preferably pyruvic acid or glyoxylic acid, although it may be of any type having activity as an amino group acceptor.

In the production method II, an enantiomeric mixture of amino compounds is allowed to react, in the presence of the amino group acceptor, with the polypeptide of the invention or a culture of a transformant having the ability to produce the polypeptide.

As used therein, the term "enantiomeric mixture of amino compounds" refers to a mixture of an enantiomer and the corresponding optical isomer. In general, a racemic mixture is preferably used because it is inexpensive and easily available. However, the amino compound is not limited to a racemic mixture, and, for example, a mixture containing an enantiomer in an amount slightly larger than that of the corresponding optical isomer may be used so that the optical purity can be advantageously increased using the production method II.

The term "culture" has the same meaning as in the case of the production method I.

The concentration of the amino compound in the liquid composition for the reaction may be 0.1 to 80% by weight, preferably 1 to 50% by weight. The concentration of the amino group acceptor may be 30 to 100% by mole, preferably 50 to 60% by mole, based on the amount of the amino compound. The same conditions for the reaction pH, the reaction temperature, and the reaction solvent as in the production method I may be used.

The reaction produces an optical active amino compound. The produced optically active amino compound may be isolated from the liquid reaction mixture using the same method as in the production method I.

EXAMPLES

Hereinafter, the invention will be more specifically described with reference to examples, which however are not intended to limit the invention.

Example 1

Preparation of Enzyme Mutant Library

A plasmid pNTMTA containing an aminotransferase (MTA) gene derived from *Pseudomonas fluorescens* strain KNK08-18 described in WO 2006/126498 A1 was used as a template together with primer 1:
5'-TGGAGTGGCCATATGAACAGCAACAACAAAGC-3' (SEQ ID NO: 3 in the Sequence Listing) and primer 2:
5'-TGGTCAGCGAATTCTTACCAGGGGTTGGCAACG-3' (SEQ ID NO: 4 in the Sequence Listing) in error prone PCR (Leung et al., Technique 1, 11-15, 1989), so that amplified DNA fragments were obtained by random mutagenesis of the MTA gene.

The amplified fragments were digested with restriction enzymes NdeI and EcoRI and then inserted into a high-expression vector pUCNT (WO 94/03613) treated with the same enzymes, so that a mixture of different mutated enzyme expression plasmids was obtained. *E. coli* HB101 was transformed with the plasmid mixture and then applied to an LB plate medium containing 100 µg/mL of ampicillin. The grown colony was recombinant *E. coli* having the mutated MTA gene, and the recombinant *E. coli* population was used as an enzyme mutant library.

Example 2

Selection (1) of Modified Aminotransferase with Higher Resistance to (S)-7-methoxy-2-aminotetralin The enzyme mutant library prepared in Example 1 was streaked on an LB plate medium containing 100 μg/mL of ampicillin, and the grown *E. coli* was inoculated on an LB plate medium containing 4% of (S)-7-methoxy-2-aminotetralin hydrochloride. Strains maintaining aminotransferase activity change into black by producing an unstable compound, 7-methoxy-2-tetralone. After the inoculation on the plate, the medium was incubated at 37° C. overnight. As a result, the wild-type enzyme lost its enzyme activity and did not change in color, but some colored strains were observed in the enzyme mutant library, and it was considered that the modified enzymes of these strains could have (S)-7-methoxy-2-aminotetralin resistance higher than that of the wild-type. These strains were inoculated into a 2×YT medium containing 200 g/mL of ampicillin, and plasmids were extracted from the resulting bacterial cells. The DNA sequences of the extracted plasmids were examined, so that the modified amino acid sequences were determined. Table 1 shows the results.

TABLE 1

| Plasmid name | Mutation site | Coloration |
|---|---|---|
| pNTMTAm01 | M161T/I418L | + |
| pNTMTAm02 | Y84C | + |
| pNTMTAm03 | M161T/V236I/I442V | + |
| pNTMTAm04 | T420S | + |
| pNTMTAm06 | M161T/T434A | ++ |
| pNTMTAm07 | T420A | + |
| pNTMTAm08 | V302I | + |
| pNTMTAm09 | T435A | + |
| pNTMTAm10 | L176S | + |
| pNTMTAm12 | M17I | ++ |
| pNTMTAm13 | E11G/N151H/M161T/I262V | + |
| pNTMTAm14 | M161T/E209A/I235V | ++ |
| pNTMTAm15 | I421T | + |
| pNTMTAm16 | H42Y/S408T | + |
| pNTMTAm17 | M17L/Y153F | + |
| pNTMTAm18 | E29K/I262V | + |
| pNTMTAm19 | M161T | ++ |
| pNTMTAm20 | M161V | + |
| pNTMTAm21 | M161T/M248I | + |
| pNTMTAm22 | M17L | + |
| pNTMTAm23 | S3R/M17L/F116L/H190Y | + |
| pNTMTA | (Wild-type enzyme) | − |

Example 3

Selection (1) of Modified Aminotransferase with Higher Stereoselectivity; Stereoselectivity for 7-Methoxy-2-Tetralone (30° C., PEA Method)

The recombinant *E. coli* obtained in Example 2 was inoculated into 5 mL of a 2×YT medium containing 200 μg/mL of ampicillin and cultured with shaking at 30° C. for 28 hours. To 500 μL of the resulting culture liquid was added 500 μL of a 0.2 M potassium phosphate buffer (pH 7.5) containing 1 mM pyridoxal phosphate, and the mixture was sonicated so that a cell-free extract was obtained. Subsequently, 100 μL of the cell-free extract was added to 305 μL of a substrate solution having the composition shown below. After the mixture was allowed to react at 30° C. for 1 hour, 50 μL of 6 N hydrochloric acid was added to stop the reaction. The optical purity of the produced (S)-7-methoxy-2-aminotetralin was measured using HPLC under the conditions shown below. As a result, the modified enzymes shown in Table 2 had stereoselectivity higher than that of the wild-type.

[The Composition of the Substrate Solution]

| | |
|---|---|
| (S)-1-phenethylamine | 21 mM |
| Potassium phosphate (pH 7.5) | 0.1 M |
| 7-methoxy-2-tetralone | 14 mM |

[Measurement Conditions for High-Performance Liquid Chromatography (HPLC)]

Column: Crownpak CR (+) (manufactured by Daicel Corporation)
Eluent: aqueous perchloric acid solution (pH 1.5)/methanol=85/15 (volume ratio)
Flow rate: 1 mL/minute
Detection: 220 nm
Column temperature: 47° C.

TABLE 2

| Plasmid name | Mutation site | Optical purity |
|---|---|---|
| pNTMTAm01 | M161T/I418L | 98.8% |
| pNTMTAm04 | T420S | 98.7% |
| pNTMTAm15 | I421T | 98.7% |
| pNTMTAm07 | T420A | 98.6% |
| pNTMTAm21 | M161T/M284I | 98.6% |
| pNTMTAm03 | M161T/V236I/I442V | 98.5% |
| pNTMTAm19 | M161T | 98.5% |
| pNTMTAm10 | L176S | 98.4% |
| pNTMTAm14 | M161T/E209A/I235V | 98.3% |
| pNTMTAm05 | M161T | 98.1% |
| pNTMTAm06 | M161T/T434A | 98.1% |
| pNTMTAm16 | H42Y/S408T | 97.9% |
| pNTMTAm02 | Y84C | 97.8% |
| pNTMTAm22 | M17L | 97.8% |
| pNTMTAm20 | M161V | 97.7% |
| pNTMTAm12 | M17I | 97.6% |
| pNTMTAm18 | E29K/I262V | 97.6% |
| pNTMTAm13 | E11G/N151H/M161T/I262V | 97.5% |
| pNTMTA | (Wild-type enzyme) | 97.3% |

Example 4

Selection (2) of Modified Aminotransferase with Higher Resistance to (S)-7-methoxy-2-aminotetralin (6%)

A liquid culture of each mutant strain was obtained using the same process as in Example 3. After 5 mL of the liquid culture was centrifuged to give bacterial cells, 1 mL of a 100 mM potassium phosphate buffer (pH 7.5) containing 0.5 mM of pyridoxal phosphate was added to the bacterial cells. The mixture was sonicated so that a cell-free extraction was obtained.

To a test tube were added 50 μL of the cell-free extract, 600 μL of an aqueous solution of 10% (S)-7-methoxy-2-aminotetralin hydrochloride, 100 μL of an aqueous 0.46 M sodium pyruvate solution (pH 7.5), 50 μL of a 1 M MOPS buffer (pH 7.5), 10 μL of an aqueous 50 mM PLP solution (pH 7.5), and 190 μL of water. After argon gas was injected, the tube was hermetically sealed, and the mixture was agitated with a stirrer at 30° C. for 4 hours. The mixture was sampled in an amount of 200 μL, and 50 μL of 0.6 N hydrochloric acid was added to the sample to stop the reaction. The concentration of the produced 7-methoxy-2-tetralone was measured using HPLC under the conditions shown below, when the activity was determined. As a result, the modified enzymes shown in Table 3 had remaining activity higher than that of the wild-type enzyme and had (S)-7-methoxy-2-aminotetralin resistance higher than that of the wild-type.

[Measurement Conditions for High-Performance Liquid Chromatography (HPLC)]

<Quantitative Analysis>

Column: Cosmosil 5C8-MS (manufactured by NACALAI TESQUE, INC.)

Eluent: 30 mM potassium phosphate buffer (pH 2.5)/acetonitrile/methanol=4/1/1 (volume ratio)

Flow rate: 0.9 mL/minute

Detection: 254 nm

TABLE 3

| Plasmid name | Mutation site | Remaining activity (%) |
|---|---|---|
| pNTMTAm03 | M161T/V236I/I442V | 89.1% |
| pNTMTAm06 | M161T/T434A | 85.8% |
| pNTMTAm14 | M161T/E209A/I235V | 78.1% |
| pNTMTAm10 | L176S | 73.2% |
| pNTMTAm19 | M161T | 69.3% |
| pNTMTAm01 | M161T/I418L | 59.8% |
| pNTMTAm12 | M17I | 57.9% |
| pNTMTAm21 | M161T/M284I | 52.3% |
| pNTMTAm17 | M17L/Y153F | 43.4% |
| pNTMTAm13 | E11G/N151H/M161T/I262V | 38.0% |
| pNTMTAm23 | S3R/M17L/F116L/H190Y | 21.8% |
| pNTMTAm02 | Y84C | 20.7% |
| pNTMTAm08 | V302I | 19.3% |
| pNTMTAm20 | M161V | 18.3% |
| pNTMTAm11 | S171R | 16.0% |
| pNTMTAm22 | M17L | 10.7% |
| pNTMTAm18 | E29K/I262V | 10.3% |
| pNTMTAm07 | T420A | 8.2% |
| pNTMTAm04 | T420S | 7.0% |
| pNTMTA | (Wild-type enzyme) | 5.4% |

Example 5

Selection (3) of Modified Aminotransferase with Higher Resistance to (S)-7-methoxy-2-aminotetralin (0.9%)

A liquid culture of each mutant strain was obtained using the same process as in Example 2. After 8 mL of the culture was centrifuged to give bacterial cells, 1 mL of a 30 mM potassium phosphate buffer (pH 6.1) containing 0.5 mM of pyridoxal phosphate was added to the bacterial cells. The mixture was sonicated so that a cell-free extraction was obtained. To 100 μL of the cell-free extract was added 900 μL of a 0.1 M potassium phosphate buffer (pH 6.3) containing 1% of (S)-7-methoxy-2-aminotetralin hydrochloride, and the mixture was incubated at 35° C. The mixture was sampled in an amount of 100 μL at reaction times 0 and 20 hours, respectively, and each sample was diluted 200 times with an aqueous 0.1 M potassium phosphate solution (pH 7.5). Subsequently, 200 μL of each dilution was added to 800 μL of a substrate solution having the composition shown below. After the mixture was allowed to react at 30° C. for 1 hour, 50 μL of 6 N hydrochloric acid was added to stop the reaction. The concentration of the produced acetophenone was measured using HPLC under the same conditions as in Example 4. The remaining activity at reaction time 20 hours was determined relative to the activity at reaction time 0, which was normalized as 100%. The modified enzymes shown in Table 4 had (S)-7-methoxy-2-aminotetralin resistance higher than that of the wild-type.

[The Composition of the Substrate Solution]

| | |
|---|---|
| (S)-1-phenethylamine | 25 mM |
| Sodium pyruvate | 25 mM |
| Pyridoxal phosphate | 2.5 mM |
| Tris (pH 8.5) | 0.1M |

TABLE 4

| Plasmid name | Mutation site | Remaining activity (%) |
|---|---|---|
| pNTMTAm19 | M161T | 97.2% |
| pNTMTAm17 | M17L/Y153F | 87.8% |
| pNTMTAm06 | M161T/T434A | 95.2% |
| pNTMTAm12 | M17I | 86.0% |
| pNTMTAm14 | M161T/E209A/I235V | 84.2% |
| pNTMTAm03 | M161T/V236I/I442V | 82.1% |
| pNTMTAm21 | M161T/M284I | 75.4% |
| pNTMTAm01 | M161T/I418L | 78.8% |
| pNTMTAm08 | V302I | 44.5% |
| pNTMTAm22 | M17L | 41.6% |
| pNTMTAm20 | M161V | 45.9% |
| pNTMTAm15 | I421T | 38.3% |
| pNTMTAm07 | T420A | 41.0% |
| pNTMTAm04 | T420S | 38.5% |
| pNTMTAm23 | S3R/M17L/F116L/H190Y | 46.6% |
| pNTMTAm18 | E29K/I262V | 28.8% |
| pNTMTAm16 | H42Y/S408T | 20.7% |
| pNTMTAm11 | S171R | 36.5% |
| pNTMTAm09 | T435A | 27.0% |
| pNTMTAm13 | E11G/N151H/M161T/I262V | 17.1% |
| pNTMTA | (Wild-type enzyme) | 7.4% |

Example 6

Selection (1) of Modified Aminotransferase with Enhanced Activity (30° C. PEA Method)

A cell-free extract of each mutant strain was obtained using the same process as in Example 2. To a test tube were added 50 μL of the cell-free extract, 150 μL of a 0.1 M potassium phosphate buffer (pH 7.5) containing 1 mM of pyridoxal phosphate, 200 μL of a 0.1 M potassium phosphate buffer (pH 7.5) containing 42 mM of (S)-1-phenethylamine, and 5 μL of a DMSO solution containing 20% of 7-methoxy-2-tetralone. After argon gas was injected, the tube was hermetically sealed, and the mixture was agitated with a stirrer at 30° C. for 1 hour. Subsequently, 50 μL of 6 N hydrochloric acid was added to stop the reaction, and the concentration of the produced (S)-7-methoxy-2-aminotetralin was measured by the same method using high-performance liquid chromatography as in Example 4, when the activity was determined. As a result, the modified enzymes shown in Table 5 had activity higher than that of the wild-type.

TABLE 5

| Plasmid name | Mutation site | Relative activity |
|---|---|---|
| pNTMTAm02 | Y84C | 249% |
| pNTMTAm04 | T420S | 178% |
| pNTMTAm15 | I421T | 154% |
| pNTMTAm22 | M17L | 124% |
| pNTMTAm07 | T420A | 101% |
| pNTMTA | (Wild-type enzyme) | 100% |

Example 7

Selection (1) of Modified Aminotransferase of which Product

(S)-7-methoxy-2-aminotetralin-Induced Competitive Inhibition is Reduced (30° C. PEA Method)

A liquid culture of each mutant strain was obtained using the same process as in Example 2. After 5 mL of the culture was centrifuged to give bacterial cells, 1 mL of a 100 mM potassium phosphate buffer (pH 7.5) containing 0.5 mM of pyridoxal phosphate was added to the bacterial cells. The mixture was sonicated so that a cell-free extract was obtained. To a test tube were added 100 μL of the cell-free extract, 600 μL of an aqueous solution of 10% (S)-7-methoxy-2-aminotetralin hydrochloride, 100 μL of an aqueous 1.13 M (S)-1-phenethylamine solution (pH 7.5), 50 μL of a 1 M MOPS buffer (pH 7.5), 10 μL of an aqueous 50 mM PLP solution (pH 7.5), 10 mg of 7-methoxy-2-tetralone, and 130 μL of water. After argon gas was injected, the tube was hermetically sealed, and the mixture was agitated with a stirrer at 30° C. for 1 hour. The mixture was sampled in an amount of 200 μL, and 50 μL of 0.6 N hydrochloric acid was added to the sample to stop the reaction. The concentration of the produced acetophenone was measured using HPLC under the same conditions as in Example 4, when the activity was determined. As a result, the product (S)-7-methoxy-2-aminotetralin-induced competitive inhibition of the modified enzymes shown in Table 6 was lower than that of the wild-type enzyme.

TABLE 6

| Plasmid name | Mutation site | Relative activity |
| --- | --- | --- |
| pNTMTAm12 | M17I | 56% |
| pNTMTAm06 | M161T/T434A | 53% |
| pNTMTAm10 | L176S | 49% |
| pNTMTAm05 | M161T | 49% |
| pNTMTAm03 | M161T/V236I/I442V | 35% |
| pNTMTAm14 | M161T/E209A/I235V | 33% |
| pNTMTAm17 | M17L/Y153F | 22% |
| pNTMTAm01 | M161T/I418L | 20% |
| pNTMTAm13 | M161T/E11G/N151H/I262V | 20% |
| pNTMTAm21 | M161T/M284I | 18% |
| pNTMTAm11 | S171R | 16% |
| pNTMTAm08 | V302I | 16% |
| pNTMTAm20 | M161V | 13% |
| pNTMTAm09 | T435A | 10% |
| pNTMTA | (Wild-type enzyme) | 9% |

Example 8

Selection (1) of Modified Aminotransferase with Higher Heat Resistance

*E. coli* HB101 was transformed with the plasmid mixture prepared in Example 1, and the transformant was applied to an LB plate medium containing 100 μg/mL of ampicillin. The grown colony was adsorbed onto a sterilized filter paper. The filter paper was heated in hot water at 75° C. for 5 minutes and then cooled to room temperature. The filter paper was immersed in a reactive solution having the composition shown below. After the reaction was performed at 37° C. for 5 hours, strains, for which coloration was observed, were obtained from the corresponding colonies on the original LB plate. These strains were cultured in an LB medium, and the DNA sequences of the extracted plasmids were examined, so that the modified amino acid sequences were determined. As a result, the modified enzymes having the mutation shown in Table 7 had heat resistance higher than that of the wild-type enzyme.

[The Composition of the Substrate Solution]

| | |
| --- | --- |
| (S)-7-methoxy-2-aminotetralin | 56 mM |
| Sodium pyruvate | 84 mM |
| Potassium phosphate (pH 7.5) | 0.1 M |

TABLE 7

| Plasmid name | Mutation site | Coloration |
| --- | --- | --- |
| pNTMTAm22 | M17L | + |
| pNTMTAm23 | S3R/M17L/F116L/H190Y | + |
| pNTMTA | (Wild-type enzyme) | − |

Example 9

Selection (2) of Modified Aminotransferase with Higher Heat Resistance

The recombinant *E. coli* obtained in Example 8 was inoculated into 5 mL of a 2×YT medium containing 200 μg/mL of ampicillin and cultured with shaking at 30° C. for 28 hours. Bacterial cells were obtained by centrifuging 1 mL of the resulting culture. To the bacterial cells was added 1 mL of a 0.1 M potassium phosphate buffer (pH 7.0) containing 0.5 mM of pyridoxal phosphate, and the mixture was sonicated so that a cell-free extract was obtained. After 500 μL of the cell-free extract was incubated at 75° C. for 30 minutes, the cell-free extract was cooled to 4° C. The heat-treated, cell-free extract and the cell-free extract before the heat treatment were measured for the activity by the same method as in Example 5, and the activity residual rate after the heat treatment of the enzyme was determined. As a result, the modified enzymes shown in Table 8 had heat resistance higher than that of the wild-type.

TABLE 8

| Plasmid name | Mutation site | Activity residual rate (%) |
| --- | --- | --- |
| pNTMTAm22 | M17L | 45 |
| pNTMTAm23 | S3R/M17L/F116L/H190Y | 89 |
| pNTMTA | (Wild-type enzyme) | 16 |

Example 10

Preparation (1) of Multiply-Mutated, Modified Aminotransferase

The plasmid pNTMTAm04 obtained in Example 2 was used as a template together with primer 2: 5'-TGGTCAGC-GAATTCTTACCAGGGGTTGGCAACG-3' (SEQ ID NO: 4 in the Sequence Listing) and primer 3: 5'-GAAGAGCTGGCGTACTGTTCGTTGTTTCCCGGC-3' (SEQ ID NO: 5 in the Sequence Listing), and primer 1: 5'-TGGAGTGGCCATATGAACAGCAACAACAAAGC-3' (SEQ ID NO: 3 in the Sequence Listing) and primer 4: 5'-GCCGGGAAACAACGAACAGTACGCCAGCTCTTC-3' (SEQ ID NO: 6 in the Sequence Listing) in PCR, respectively, so that amplified DNA fragments were obtained. The resulting amplified DNA fragments were mixed. The mixture was used as a template together with primers 1 and 2 in PCR, so that double stranded DNA encoding a polypeptide having the amino acid substitutions Y84C and T420S in the amino acid sequence of SEQ ID NO: 1 in the Sequence Listing was obtained. The amplified fragment was digested with restriction enzymes NdeI and EcoRI, and then inserted into a plasmid vector pUCNT (WO 94/03613) treated with the same enzymes. *E. coli* HB101 competent cells (manufactured by TAKARA BIO INC.) were transformed with the resulting plasmid vector, so that recombinant *E. coli* capable of expressing a modified enzyme having the amino acid substitutions Y84C/T420S was obtained.

Example 11

Selection (2) of Modified Aminotransferase with Higher Activity (Multiple Mutations)

The activity of the recombinant *E. coli* obtained in Example 10 was measured by the same method as in Example 6. As a result, as shown in Table 9, the double-mutated enzyme with Y84C and T420S exhibited activity higher than that of the single-mutated enzyme.

TABLE 9

| Plasmid name | Mutation site | Relative activity |
| --- | --- | --- |
| pNTMTAm25 | Y84C/T420S | 261% |
| pNTMTAm04 | T420S | 142% |
| pNTMTA | (Wild-type enzyme) | 100% |

Example 12

Preparation of Enzyme with Modified Residue 420

A plasmid pNTMTA containing an MTA gene derived from *Pseudomonas fluorescens* strain KNK08-18 described in WO 2006/126498 A1 was used as a template. A plasmid containing DNA encoding an enzyme with a modified residue at position 420 of MTA was obtained by the same process as in Example 10 using the template. Primers 1 and 2 were commonly used in the preparation of each plasmid. Besides primers 1 and 2, the following primers were used.

```
T420F primer 5:
       (SEQ ID NO: 7 in the Sequence Listing)
5'-CGGAGTGATGATTCGTTTTATCGTCAACAAGCTG-3'

Primer 6:
       (SEQ ID NO: 8 in the Sequence Listing)
5'-CAGCTTGTTGACGATAAAACGAATCATCACTCCG-3'

T420L primer 7:
       (SEQ ID NO: 9 in the Sequence Listing)
5'-CGGAGTGATGATTCGTCTGATCGTCAACAAGCTG-3'

Primer 8:
       (SEQ ID NO: 10 in the Sequence Listing)
5'-CAGCTTGTTGACGATCAGACGAATCATCACTCCG-3'

T470I primer 9:
       (SEQ ID NO: 11 in the Sequence Listing)
5'-CGGAGTGATGATTCGTATTATCGTCAACAAGCTG-3'

Primer 10:
       (SEQ ID NO: 12 in the Sequence Listing)
5'-CAGCTTGTTGACGATAATACGAATCATCACTCCG-3'

T420m primer 11:
       (SEQ ID NO: 13 in the Sequence Listing)
5'-CGGAGTGATGATTCGTATGATCGTCAACAAGCTG-3'

Primer 12:
       (SEQ ID NO: 14 in the Sequence Listing)
5'-CAGCTTGTTGACGATCATACGAATCATCACTCCG-3'

T420V primer 13:
       (SEQ ID NO: 15 in the Sequence Listing)
5'-CGGAGTGATGATTCGTGTGATCGTCAACAAGCTG-3'

Primer 14:
       (SEQ ID NO: 16 in the Sequence Listing)
5'-CAGCTTGTTGACGATCACACGAATCATCACTCCG-3'

T420A primer 15:
       (SEQ ID NO: 17 in the Sequence Listing)
5'-CGGAGTGATGATTCGTGCGATCGTCAACAAGCTG-3'

Primer 16:
       (SEQ ID NO: 18 in the Sequence Listing)
5'-CAGCTTGTTGACGATCGCACGAATCATCACTCCG-3'

T420Y primer 17:
       (SEQ ID NO: 19 in the Sequence Listing)
5'-CGGAGTGATGATTCGTTATATCGTCAACAAGCTG-3'

Primer 18:
       (SEQ ID NO: 20 in the Sequence Listing)
5'-CAGCTTGTTGACGATATAACGAATCATCACTCCG-3'

T420H primer 19:
       (SEQ ID NO: 21 in the Sequence Listing)
5'-CGGAGTGATGATTCGTCATATCGTCAACAAGCTG-3'

Primer 20:
       (SEQ ID NO: 22 in the Sequence Listing)
5'-CAGCTTGTTGACGATATGACGAATCATCACTCCG-3'

T420Q primer 21:
       (SEQ ID NO: 23 in the Sequence Listing)
5'-CGGAGTGATGATTCGTCAGATCGTCAACAAGCTG-3'

Primer 22:
       (SEQ ID NO: 24 in the Sequence Listing)
5'-CAGCTTGTTGACGATCTGACGAATCATCACTCCG-3'

T420N primer 23:
       (SEQ ID NO: 25 in the Sequence Listing)
5'-CGGAGTGATGATTCGTAACATCGTCAACAAGCTG-3'

Primer 24:
       (SEQ ID NO: 26 in the Sequence Listing)
5'-CAGCTTGTTGACGATGTTACGAATCATCACTCCG-3'

T420K primer 25;
       (SEQ ID NO: 27 in the Sequence Listing)
5'-CGGAGTGATGATTCGTAAAATCGTCAACAAGCTG-3'

Primer 26:
       (SEQ ID NO: 28 in the Sequence Listing)
5'-CAGCTTGTTGACGATTTTACGAATCATCACTCCG-3'

T420D primer 27:
       (SEQ ID NO: 29 in the Sequence Listing)
5'-CGGAGTGATGATTCGTGATATCGTCAACAAGCTG-3'

Primer 28:
       (SEQ ID NO: 30 in the Sequence Listing)
5'-CAGCTTGTTGACGATATCACGAATCATCACTCCG-3'

T420E primer 29
       (SEQ ID NO: 31 in the Sequence Listing)
5'-CGGAGTGATGATTCGTGAAATCGTCAACAAGCTG-3'

Primer 30:
       (SEQ ID NO: 32 in the Sequence Listing)
5'-CAGCTTGTTGACGATTTCACGAATCATCACTCCG-3'

T420W primer 31:
       (SEQ ID NO: 33 in the Sequence Listing)
5'-CGGAGTGATGATTCGTTGGATCGTCAACAAGCTG-3'
```

-continued

```
Primer 32:
    (SEQ ID NO: 34 in the Sequence Listing)
5'-CAGCTTGTTGACGATCCAACGAATCATCACTCCG-3'

T420R primer 33:
    (SEQ ID NO: 35 in the Sequence Listing)
5'-CGGAGTGATGATTCGTCGCATCGTCAACAAGCTG-3'

Primer 34:
    (SEQ ID NO: 36 in the Sequence Listing)
5'-CAGCTTGTTGACGATGCGACGAATCATCACTCCG-3'

T420S primer 35:
    (SEQ ID NO: 37 in the Sequence Listing)
5'-CGGAGTGATGATTCGTAGCATCGTCAACAAGCTG-3'

Primer 36:
    (SEQ ID NO: 38 in the Sequence Listing)
5'-CAGCTTGTTGACGATGCTACGAATCATCACTCCG-3'
```

Double stranded DNA that was obtained by digesting pNTTAPAG (described in WO 2007/139255) with restriction enzymes SacI and SphI and had structural genes of L-lactic acid dehydrogenase (PALDH) derived from *Pediococcus acidilactici* strain JCM8797 and glucose dehydrogenase (GDH) derived from *Bacillus megaterium* strain IAM1030, both linked together, was inserted between SacI and SphI restriction sites of each plasmid capable of expressing the enzyme having a modified residue at position 420, which was obtained in this experiment, so that pNTTAm04-01 to pNTTAm04-17 were obtained. *E. coli* HB101 competent cells (manufactured by TAKARA BIO INC.) were transformed with the resulting plasmids, so that each recombinant *E. coli* capable of coexpressing an enzyme with a modified residue at position 420, PALDH, and GDH was obtained.

Example 13

Selection (2) of Modified Aminotransferase with Higher Stereoselectivity (Evaluation of Enzyme with Modified Residue 420) (35° C., Alanine Method)

Each recombinant *E. coli*, obtained in Example 12, capable of coexpressing an enzyme with a modified residue at position 420, PALDH, and GDH was inoculated into 5 mL of a 2× YT medium containing 200 μg/mL of ampicillin and cultured with shaking at 30° C. for 28 hours. After 2 ml of the liquid culture was centrifuged to give bacterial cells, 1 mL of a 100 mM potassium phosphate buffer (pH 6.8) containing 0.5 mM of pyridoxal phosphate was added to the bacterial cells. The mixture was sonicated so that a cell-free extract was obtained. Subsequently, 250 μL of a substrate solution having the composition shown below was added to 250 μL of the cell-free extract. After the mixture was allowed to react at 35° C. for 1.5 hours, 50 μL of 6 N hydrochloric acid was added to stop the reaction. The optical purity of the produced (S)-7-methoxy-2-aminotetralin was measured using HPLC under the same conditions as in Example 2. As a result, the modified enzymes shown in Table 10 had stereoselectivity higher than that of the wild-type.

[The Composition of the Substrate Solution]

| | |
|---|---|
| Potassium phosphate (pH 6.8) | 0.2M |
| L-alanine | 1.12M |
| D-glucose | 340 mM |
| NADH | 0.2 mM |
| Pyridoxal phosphate | 0.8 mM |
| 7-methoxy-2-tetralone | 228 mM |

TABLE 10

| Plasmid name | Mutation site | Optical purity (% ee) |
|---|---|---|
| pNTTAm04-01PAG | T420D | 98.7 |
| pNTTAm04-02PAG | T420E | 98.7 |
| pNTTAm04-03PAG | T420R | 98.6 |
| pNTTAm04-04PAG | T420H | 98.5 |
| pNTTAm04-05PAG | T420Q | 98.5 |
| pNTTAm04-06PAG | T420N | 98.4 |
| pNTTAm04-07PAG | T420K | 98.3 |
| pNTTAm04-08PAG | T420A | 98.2 |
| pNTTAm04-09PAG | T420V | 98.1 |
| pNTTAm04-10PAG | T420W | 98.1 |
| pNTTAm04-11PAG | T420S | 98.0 |
| pNTTAm04-12PAG | T420I | 97.9 |
| pNTTAm04-13PAG | T420M | 97.9 |
| pNTTAm04-14PAG | T420Y | 97.5 |
| pNTTAm04-16PAG | T420L | 97.3 |
| pNTTAm04-17PAG | T420F | 97.2 |
| pNTTAPAG | (Wild-type enzyme) | 96.7 |

Example 14

Preparation (2) of Multiply-Mutated, Modified Aminotransferase (Three-Enzyme Bacterium)

The plasmids pNTMTAm12 (M17I) and pNTMTAm19 (M161T), obtained in Example 2, capable of expressing a modified enzyme were used as templates, when multiple mutagenesis was performed using the same process as in Example 10 to construct plasmids. The PALDH gene and the GDH gene were inserted into the resulting plasmids using the same process as in Example 12, so that the plasmids shown in Table 11 were constructed. *E. coli* HB101 competent cells (manufactured by TAKARA BIO INC.) were transformed with the resulting plasmids, so that each recombinant *E. coli* capable of coexpressing a modified enzyme, PALDH, and GDH was obtained.

TABLE 11

| Plasmid name | Mutation site |
|---|---|
| pNTTPAG | (Wild-type enzyme) |
| pNTTAm19PAG | M161T |
| pNTTAm12PAG | M17I |
| pNTTAm04-04PAG | T420H |
| pNTTAm26PAG | M161T/M17I |
| pNTTAm27PAG | M161T/T420H |
| pNTTAm28PAG | M17I/T420H |
| pNTTAm29PAG | M161T/M17I/T420H |

Primers 1 and 2 were commonly used in the preparation of each plasmid. Besides primers 1 and 2, the following primers were used for the preparation of modified enzymes.

```
T420H primer 19:
    (SEQ ID NO: 21 in the Sequence Listing)
5'-CGGAGTGATGATTCGTCATATCGTCAACAAGCTG-3'

Primer 20:
    (SEQ ID NO: 22 in the Sequence Listing)
5'-CAGCTTGTTGACGATATGACGAATCATCACTCCG-3'

M17I primer 37:
    (SEQ ID NO: 39 in the Sequence Listing)
5'-GCACAACACGGTGCACATTATGCATCCGATGC-3'

Primer 38:
    (SEQ ID NO: 40 in the Sequence Listing)
5'-GCATCGGATGCATAATGTGCACCGTGTTGTGC-3'
```

-continued

M161T primer 39:
    (SEQ ID NO: 41 in the Sequence Listing)
5'-GAACTTCGGTGGCACGTCCGCCTGTGGCG-3'

Primer 40:
    (SEQ ID NO: 42 in the Sequence Listing)
5'-CGCCACAGGCGGACGTGCCACCGAAGTTC-3'

Example 15

Selection (3) of Modified Aminotransferase with Higher Resistance to (S)-7-methoxy-2-aminotetralin (Multiple Mutations 0.9%. 45° C.)

A liquid culture of the recombinant *E. coli* obtained in Example 14 was prepared using the same process as in Example 13. After 8 mL of the culture was centrifuged to give bacterial cells. 1 mL of a 30 mM potassium phosphate buffer (pH 6.1) containing 0.5 mM of pyridoxal phosphate was added to the bacterial cells. The mixture was sonicated so that a cell-free extract was obtained. Subsequently, 900 µL of a 0.1 M potassium phosphate buffer (pH 6.3) containing 1% of (S)-7-methoxy-2-aminotetralin hydrochloride was added to 100 µL of the cell-free extract and incubated at 45° C. The mixture was sampled in an amount of 100 µL at reaction times 0 and 20 hours, respectively, and each sample was diluted 200 times with an aqueous 0.1 M potassium phosphate solution (pH 7.5). Subsequently, 200 µL of each dilution was added to 800 µL of a substrate solution having the composition shown below. After the mixture was allowed to react at 30° C. for 1 hour, 50 µL of 6 N hydrochloric acid was added to stop the reaction. The concentration of the produced acetophenone was measured using HPLC under the same conditions as in Example 4. Table 12 shows the remaining activity at reaction time 20 hours, which was determined relative to the activity at reaction time 0 normalized as 100%. The modified enzymes shown in the table below had (S)-7-methoxy-2-aminotetralin resistance higher than that of the wild-type.

[The Composition of the Substrate Solution]

| (S)-1-phenethylamine | 25 mM |
| Sodium pyruvate | 25 mM |
| Pyridoxal phosphate | 2.5 mM |
| Tris (pH8.5) | 0.1M |

TABLE 12

| Plasmid name | Mutation site | Remaining activity |
| --- | --- | --- |
| pNTTPAG | (Wild-type enzyme) | 8% |
| pNTTAm19PAG | M161T | 54% |
| pNTTAm12PAG | M17I | 50% |
| pNTTAm26PAG | M161T/M17I | 83% |
| pNTTAm27PAG | M161T/T420H | 64% |
| pNTTAm28PAG | M17I/T420H | 58% |
| pNTTAm29PAG | M161T/M17I/T420H | 87% |

Example 16

Selection (3) of Modified Aminotransferase with Higher Stereoselectivity (Multiple Mutations. 45° C., ALA Method)

The recombinant *E. coli* obtained in Example 14 was examined for modified enzyme stereoselectivity under the same conditions as in Example 13. As a result, the modified enzymes shown in Table 13 had stereoselectivity higher than that of the wild-type.

TABLE 13

| Plasmid name | Mutation site | Optical purity (% ee) |
| --- | --- | --- |
| pNTTPAG | (Wild-type enzyme) | 96.9 |
| pNTTAm19PAG | M161T | 98.1 |
| pNTTAm12PAG | M17I | 97.7 |
| pNTTAm04-04PAG | T420H | 98.6 |
| pNTTAm26PAG | M161T/M17I | 98.6 |
| pNTTAm27PAG | M161T/T420H | 99.0 |
| pNTTAm28PAG | M17I/T420H | 98.9 |
| pNTTAm29PAG | M161T/M17I/T420H | 99.4 |

Example 17

Stereoselectivity for N-benzyl-3-pyrrolidinone (30° C., Alanine Method)

The recombinant *E. coli* obtained in Example 14 was examined for stereoselectivity for N-benzyl-3-pyrrolidinone. A cell-free extract was obtained using the same process as in Example 13, and 250 µL of a substrate solution having the composition shown below was added to 250 µL of the cell-free extract. After the mixture was allowed to react at 30° C. for 1.5 hours, 50 µL of 6 N hydrochloric acid was added to stop the reaction. The optical purity of the produced (S)—N-benzyl-3-aminopyrrolidine was measured under the analysis conditions shown below. As a result, the mutated enzymes shown in Table 14 had higher stereoselectivity for N-benzyl-3-pyrrolidinone than the wild-type enzyme.

[The Composition of the Substrate Solution]

| Potassium phosphate (pH 6.8) | 0.2M |
| L-alanine | 1.12M |
| D-glucose | 340 mM |
| NADH | 0.2 mM |
| Pyridoxal phosphate | 0.8 mM |
| N-benzyl-3-pyrrolidinone | 228 mM |

[Optical Purity Measurement Conditions for High-Performance Liquid Chromatography (HPLC)]

The reaction liquid was adjusted to be basic with a proper amount of sodium carbonate. Subsequently, derivatization was performed with dinitrobenzoyl chloride, and then analysis was performed under the following conditions.

Column: Chiralcel IA (manufactured by Daicel Corporation)
Eluent: hexane/ethanol/diethylamine/acetonitrile=800/200/1/5 (volume ratio)
Flow rate: 0.8 mL/minute
Detection: 254 nm
Column temperature: 30° C.

TABLE 14

| Plasmid name | Mutation site | Optical purity (% ee) |
| --- | --- | --- |
| pNTTPAG | (Wild-type enzyme) | 80.3 |
| pNTTAm19PAG | M161T | 82.4 |
| pNTTAm12PAG | M17I | 84.5 |
| pNTTAm04-04PAG | T420H | 81.2 |
| pNTTAm26PAG | M161T/M17I | 83.0 |
| pNTTAm27PAG | M161T/T420H | 81.6 |
| pNTTAm28PAG | M17I/T420H | 83.8 |
| pNTTAm29PAG | M161T/M17I/T420H | 83.8 |

Example 18

Stability to (S)—N-benzyl-3-aminopyrrolidine (30° C. Alanine Method)

The recombinant E. coli obtained in Example 14 was examined for resistance to (S)—N-benzyl-3-aminopyrrolidinone. A cell-free extract of each multiply-mutated strain was obtained using the same process as in Example 13. Subsequently, 900 μL of a 0.1 M potassium phosphate buffer (pH 6.3) containing 0.83% of (S)—N-benzyl-3-aminopyrrolidinone was added to 100 μL of the cell-free extract and incubated at 35° C. The mixture was sampled in an amount of 100 μL at reaction times 0 and 2.5 hours, respectively, and each sample was diluted 200 times with an aqueous 0.1 M potassium phosphate solution (pH 7.5). Subsequently, 200 μL of each dilution was added to 800 μL of a substrate solution having the composition shown below. After the mixture was allowed to react at 30° C. for 1 hour, 50 μL of 6 N hydrochloric acid was added to stop the reaction. The concentration of the produced acetophenone was measured using HPLC under the same conditions as in Example 4. Table 15 shows the remaining activity at reaction time 2.5 hours, which was determined relative to the activity at reaction time 0 normalized as 100%. As a result, the mutated enzymes shown in Table 15 had (S)-7-methoxy-2-aminotetralin resistance higher than that of the wild-type enzyme.

TABLE 15

| Plasmid name | Mutation site | Remaining activity (%) |
| --- | --- | --- |
| pNTTPAG | (Wild-type enzyme) | 56 |
| pNTTAm19PAG | M161T | 80 |
| pNTTAm12PAG | M17I | 100 |
| pNTTAm26PAG | M161T/M17I | 82 |
| pNTTAm27PAG | M161T/T420H | 100 |
| pNTTAm28PAG | M17I/T420H | 78 |
| pNTTAm29PAG | M161T/M17I/T420H | 89 |

Example 19

35° C., WT (Wild-Type) and M161T

To a 100 mL three-neck flask were added 1.6 g of 7-methoxy-2-tetralone, 4.85 g of L-alanine, 2.45 g of D-glucose, 6.5 mg of NAD, and 60.2 mg of pyridoxal phosphate in advance. To the flask was added 40 mL of a broth of the wild-type enzyme or M161T obtained in Example 18. While the mixture was adjusted to pH 5.7 with 3 N NaOH, the mixture was allowed to react with stirring at 35° C. for 46 hours under argon-substituted conditions. After the reaction was completed, 7-methoxy-2-tetralin produced in the reaction liquid was analyzed using HPLC as shown below. As a result, the reaction with the wild-type enzyme stopped at a conversion rate of 35%, whereas the conversion rate with M161T reached 90%. The optical purity of the produced (S)-7-methoxy-2-aminotetralin was 96.7% e.e. in the former case and 97.4% e.e. in the latter case. The remaining activity of the aminotransferase was 11% in the former case and 35% in the latter case.

[Measurement Conditions for High-Performance Liquid Chromatography]
<Quantitative Analysis>
Column: Cosmosil 5C8-MS (manufactured by NACALAI TESQUE, INC.)
Eluent: 30 mM potassium phosphate buffer (pH 2.5)/acetonitrile/methanol=4/1/1 (volume ratio)
Flow rate: 0.9 mL/minute
Detection: 254 nm
<Optical Purity Analysis>
Column: Crownpak CR (+) (manufactured by Daicel Corporation)
Eluent: aqueous perchloric acid solution (pH 1.5)/methanol=85/15 (volume ratio)
Flow rate: 0.9 mL/minute
Detection: 220 nm
Column temperature: 47° C.

Example 20

45° C., 5% Addition, WT and M161T

To a 100 mL three-neck flask were added 2.0 g of 7-methoxy-2-tetralone, 6.07 g of L-alanine, 3.07 g of D-glucose, 8.14 mg of NAD, and 75.2 mg of pyridoxal phosphate in advance. To the flask was added 40 mL of a broth of the wild-type enzyme or M161T obtained in Example 18. While the mixture was adjusted to pH 6.2 with 3 N NaOH, the mixture was allowed to react with stirring at 45° C. under argon-substituted conditions. After the reaction was performed for 24 hours, the reaction liquid was analyzed using HPLC as shown below. As a result, the reaction with the wild-type stopped at a conversion rate of 85%, whereas the conversion rate with M161T reached 96%. The optical purity of the produced (S)-7-methoxy-2-aminotetralin was 94.2% e.e. and 96.2% e.e. in these cases, respectively. The remaining activity of the aminotransferase was 20% in the former case and 40% in the latter case.

[Measurement Conditions for High-Performance Liquid Chromatography (HPLC)]
<Quantitative Analysis>
Column: Cosmosil 5C8-MS (manufactured by NACALAI TESQUE, INC.)
Eluent: 30 mM potassium phosphate buffer (pH 2.5)/acetonitrile/methanol=4/1/1 (volume ratio)
Flow rate: 0.9 mL/minute
Detection: 254 nm
<Optical Purity Analysis>
Column: Crownpak CR (+) (manufactured by Daicel Corporation)
Eluent: aqueous perchloric acid solution (pH 1.5)/methanol=85/15 (volume ratio)
Flow rate: 0.9 mL/minute
Detection: 220 nm
Column temperature: 47° C.

The invention claimed is:

1. A polypeptide having the following properties (i) to (iii):
(i) having at least 85% sequence identity to the amino acid sequence of SEQ ID NO: 1, wherein one or more amino acids have been substituted, deleted or inserted in said sequence;
(ii) being capable of catalyzing a reaction of 7-methoxy-2-tetralone to produce (S)-7-methoxy-2-aminotetralin in the presence of an amino group donor; and
(iii) having greater enzymatic catalytic activity than that of an aminotransferase consisting of the amino acid sequence of SEQ ID NO: 1.

2. A polypeptide selected from the group consisting of the following (A) to (C):
   (A) a polypeptide that consists of the amino acid sequence of SEQ ID NO: 1, wherein one or more amino acids have been substituted at one or more positions selected from positions 161, 420, 17, 84, 171, 176, 262, 302, 421, 435, 29, 42, 116, 153, 190, 284, 209, 235, 236, 408, 418, 434, 442, 3, 11, and 151;
   (B) a polypeptide that consists of an amino acid sequence in which one or more amino acids have been substituted at one or more positions selected from positions 161, 420, 17, 84, 171, 176, 262, 302, 421, 435, 29, 42, 116, 153, 190, 284, 209, 235, 236, 408, 418, 434, 442, 3, 11, and 151, and one or more amino acids at one or more positions other than the above amino acid positions has been substituted, added, inserted, or deleted in the amino acid sequence of SEQ ID NO: 1, and that is capable of catalyzing a reaction of 7-methoxy-2-tetralone to produce (S)-7-methoxy-2-aminotetralin in the presence of an amino group donor, and has reactivity higher than that of an aminotransferase consisting of the amino acid sequence of SEQ ID NO: 1; and
   (C) a polypeptide that consists of the amino acid sequence in which one or more amino acids have been substituted at one or more positions selected from positions 161, 420, 17, 84, 171, 176, 262, 302, 421, 435, 29, 42, 116, 153, 190, 284, 209, 235, 236, 408, 418, 434, 442, 3, 11, and 151 in the amino acid sequence of SEQ ID NO: 1, and a sequence identity to the amino acid sequence of SEQ ID NO: 1, except for the above substituted position or positions, is at least 85%, and that is capable of catalyzing a reaction of 7-methoxy-2-tetralone to produce (S)-7-methoxy-2-aminotetralin in the presence of an amino group donor, and has greater enzymatic catalytic activity than that of an aminotransferase consisting of the amino acid sequence of SEQ ID NO: 1.

3. The polypeptide according to claim 1, which has one or more amino acid substitutions selected from the group consisting of:
   a substitution of an uncharged amino acid or a nonpolar amino acid for a residue at position 161 in the amino acid sequence of SEQ ID NO: 1;
   a substitution of an amino acid other than proline, glycine, cysteine, and threonine for a residue at position 420 in the amino acid sequence of SEQ ID NO: 1;
   a substitution of a nonpolar amino acid for a residue at position 17 in the amino acid sequence of SEQ ID NO: 1;
   a substitution of an uncharged amino acid for a residue at position 84 in the amino acid sequence of SEQ ID NO: 1;
   a substitution of a basic amino acid for a residue at position 171 in the amino acid sequence of SEQ ID NO: 1;
   a substitution of an uncharged amino acid for a residue at position 176 in the amino acid sequence of SEQ ID NO: 1;
   a substitution of a nonpolar amino acid for a residue at position 262 in the amino acid sequence of SEQ ID NO: 1;
   a substitution of a nonpolar amino acid for a residue at position 302 in the amino acid sequence of SEQ ID NO: 1;
   a substitution of an uncharged amino acid for a residue at position 421 in the amino acid sequence of SEQ ID NO: 1;
   a substitution of a nonpolar amino acid for a residue at position 435 in the amino acid sequence of SEQ ID NO: 1;
   a substitution of a basic amino acid for a residue at position 29 in the amino acid sequence of SEQ ID NO: 1;
   a substitution of an uncharged amino acid for a residue at position 42 in the amino acid sequence of SEQ ID NO: 1;
   a substitution of a nonpolar amino acid for a residue at position 116 in the amino acid sequence of SEQ ID NO: 1;
   a substitution of a nonpolar amino acid for a residue at position 153 in the amino acid sequence of SEQ ID NO: 1;
   a substitution of a nonpolar amino acid for a residue at position 190 in the amino acid sequence of SEQ ID NO: 1;
   a substitution of an uncharged amino acid for a residue at position 284 in the amino acid sequence of SEQ ID NO: 1;
   a substitution of a nonpolar amino acid for a residue at position 209 in the amino acid sequence of SEQ ID NO: 1;
   a substitution of a nonpolar amino acid for a residue at position 235 in the amino acid sequence of SEQ ID NO: 1;
   a substitution of a nonpolar amino acid for a residue at position 236 in the amino acid sequence of SEQ ID NO: 1;
   a substitution of an uncharged amino acid for a residue at position 408 in the amino acid sequence of SEQ ID NO: 1;
   a substitution of an uncharged amino acid for a residue at position 418 in the amino acid sequence of SEQ ID NO: 1;
   a substitution of a nonpolar amino acid for a residue at position 434 in the amino acid sequence of SEQ ID NO: 1;
   a substitution of a nonpolar amino acid for a residue at position 442 in the amino acid sequence of SEQ ID NO: 1;
   a substitution of a basic amino acid for a residue at position 3 in the amino acid sequence of SEQ ID NO: 1;
   a substitution of an uncharged amino acid for a residue at position 11 in the amino acid sequence of SEQ ID NO: 1; and
   a substitution of a basic amino acid for a residue at position 151 in the amino acid sequence of SEQ ID NO: 1.

4. The polypeptide according to claim 1, which has one or more amino acid substitutions selected from the group consisting of:
   a substitution of threonine or valine for a residue at position 161 in the amino acid sequence of SEQ ID NO: 1;
   a substitution of histidine, serine, alanine, aspartic acid, glutamic acid, arginine, glutamine, asparagine, lysine, valine, or tryptophan for a residue at position 420 in the amino acid sequence of SEQ ID NO: 1;
   a substitution of isoleucine or leucine for a residue at position 17 in the amino acid sequence of SEQ ID NO: 1;
   a substitution of cysteine for a residue at position 84 in the amino acid sequence of SEQ ID NO: 1;
   a substitution of arginine for a residue at position 171 in the amino acid sequence of SEQ ID NO: 1;
   a substitution of serine for a residue at position 176 in the amino acid sequence of SEQ ID NO: 1;
   a substitution of valine for a residue at position 262 in the amino acid sequence of SEQ ID NO: 1;

a substitution of isoleucine for a residue at position 302 in the amino acid sequence of SEQ ID NO: 1;
a substitution of threonine for a residue at position 421 in the amino acid sequence of SEQ ID NO: 1;
a substitution of alanine for a residue at position 435 in the amino acid sequence of SEQ ID NO: 1;
a substitution of lysine for a residue at position 29 in the amino acid sequence of SEQ ID NO: 1;
a substitution of tyrosine for a residue at position 42 in the amino acid sequence of SEQ ID NO: 1;
a substitution of leucine for a residue at position 116 in the amino acid sequence of SEQ ID NO: 1;
a substitution of phenylalanine for a residue at position 153 in the amino acid sequence of SEQ ID NO: 1;
a substitution of tyrosine for a residue at position 190 in the amino acid sequence of SEQ ID NO: 1;
a substitution of isoleucine for a residue at position 284 in the amino acid sequence of SEQ ID NO: 1;
a substitution of alanine for a residue at position 209 in the amino acid sequence of SEQ ID NO: 1;
a substitution of valine for a residue at position 235 in the amino acid sequence of SEQ ID NO: 1;
a substitution of isoleucine for a residue at position 236 in the amino acid sequence of SEQ ID NO: 1;
a substitution of threonine for a residue at position 408 in the amino acid sequence of SEQ ID NO: 1;
a substitution of leucine for a residue at position 418 in the amino acid sequence of SEQ ID NO: 1;
a substitution of alanine for a residue at position 434 in the amino acid sequence of SEQ ID NO: 1;
a substitution of valine for a residue at position 442 in the amino acid sequence of SEQ ID NO: 1;
a substitution of arginine for a residue at position 3 in the amino acid sequence of SEQ ID NO: 1;
a substitution of glycine for a residue at position 11 in the amino acid sequence of SEQ ID NO: 1; and
a substitution of histidine for a residue at position 151 in the amino acid sequence of SEQ ID NO: 1.

5. The polypeptide according to claim 1, which has amino acid substitutions of at least one type selected from the group consisting of the following types (1) to (15):
(1) a substitution of an uncharged amino acid for a residue at position 161, a substitution of a nonpolar amino acid for a residue at position 17, and a substitution of histidine, serine, alanine, aspartic acid, or glutamic acid for a residue at position 420 in the amino acid sequence of SEQ ID NO: 1;
(2) a substitution of an uncharged amino acid for a residue at position 161 and a substitution of an uncharged amino acid for a residue at position 418 in the amino acid sequence of SEQ ID NO: 1;
(3) a substitution of an uncharged amino acid for a residue at position 161, a substitution of a nonpolar amino acid for a residue at position 236, and a substitution of a nonpolar amino acid for a residue at position 442 in the amino acid sequence of SEQ ID NO: 1;
(4) a substitution of an uncharged amino acid for a residue at position 161 and a substitution of a nonpolar amino acid for a residue at position 434 in the amino acid sequence of SEQ ID NO: 1;
(5) a substitution of an uncharged amino acid for a residue at position 11, a substitution of a basic amino acid for a residue at position 151, a substitution of an uncharged amino acid for a residue at position 161, and a substitution of a nonpolar amino acid for a residue at position 262 in the amino acid sequence of SEQ ID NO: 1;
(6) a substitution of an uncharged amino acid for a residue at position 161, a substitution of a nonpolar amino acid for a residue at position 209, and a substitution of a nonpolar amino acid for a residue at position 235 of in the amino acid sequence SEQ ID NO: 1;
(7) a substitution of an uncharged amino acid for a residue at position 42 and a substitution of an uncharged amino acid for a residue at position 408 in the amino acid sequence of SEQ ID NO: 1;
(8) a substitution of a nonpolar amino acid for a residue at position 17 and a substitution of a nonpolar amino acid for a residue at position 153 in the amino acid sequence of SEQ ID NO: 1;
(9) a substitution of a basic amino acid for a residue at position 29 and a substitution of a nonpolar amino acid for a residue at position 262 in the amino acid sequence of SEQ ID NO: 1;
(10) a substitution of an uncharged amino acid for a residue at position 161 and a substitution of an uncharged amino acid for a residue at position 284 in the amino acid sequence of SEQ ID NO: 1;
(11) a substitution of a basic amino acid for a residue at position 3, a substitution of a nonpolar amino acid for a residue at position 17, a substitution of a nonpolar amino acid for a residue at position 116, and a substitution of a nonpolar amino acid for a residue at position 190 in the amino acid sequence of SEQ ID NO: 1;
(12) a substitution of an uncharged amino acid for a residue at position 84 and a substitution of an uncharged amino acid other than threonine for a residue at position 420 in the amino acid sequence of SEQ ID NO: 1;
(13) a substitution of an uncharged amino acid for a residue at position 161 and a substitution of a nonpolar amino acid for a residue at position 17 in the amino acid sequence of SEQ ID NO: 1;
(14) a substitution of an uncharged amino acid for a residue at position 161 and a substitution of a basic amino acid for a residue at position 420 in the amino acid sequence of SEQ ID NO: 1; and
(15) a substitution of a nonpolar amino acid for a residue at position 17 and a substitution of a basic amino acid for a residue at position 420 in the amino acid sequence of SEQ ID NO: 1.

6. The polypeptide according to claim 1, which has amino acid substitutions of at least one type selected from the group consisting of the following types (16) to (30):
(16) a substitution of isoleucine for a residue at position 17, a substitution of threonine for a residue at position 161, and a substitution of histidine for a residue at position 420 in the amino acid sequence of SEQ ID NO: 1;
(17) a substitution of threonine for a residue at position 161 and a substitution of leucine for a residue at position 418 in the amino acid sequence of SEQ ID NO: 1;
(18) a substitution of threonine for a residue at position 161, a substitution of isoleucine for a residue at position 236, and a substitution of valine for a residue at position 442 in the amino acid sequence of SEQ ID NO: 1;
(19) a substitution of threonine for a residue at position 161 and a substitution of alanine for a residue at position 434 in the amino acid sequence of SEQ ID NO: 1;
(20) a substitution of glycine for a residue at position 11, a substitution of histidine for a residue at position 151, a substitution of threonine for a residue at position 161, and a substitution of valine for a residue at position 262 in the amino acid sequence of SEQ ID NO: 1;
(21) a substitution of threonine for a residue at position 161, a substitution of alanine for a residue at position 209, and a substitution of valine for a residue at position 235 in the amino acid sequence of SEQ ID NO: 1;

(22) a substitution of tyrosine for a residue at position 42 and a substitution of threonine for a residue at position 408 in the amino acid sequence of SEQ ID NO: 1;

(23) a substitution of leucine for a residue at position 17 and a substitution of phenylalanine for a residue at position 153 in the amino acid sequence of SEQ ID NO: 1;

(24) a substitution of lysine for a residue at position 29 and a substitution of valine for a residue at position 262 in the amino acid sequence of SEQ ID NO: 1;

(25) a substitution of threonine for a residue at position 161 and a substitution of isoleucine for a residue at position 284 in the amino acid sequence of SEQ ID NO: 1;

(26) a substitution of arginine for a residue at position 3, a substitution of leucine for a residue at position 17, a substitution of leucine for a residue at position 116, and a substitution of tyrosine for a residue at position 190 in the amino acid sequence of SEQ ID NO: 1;

(27) a substitution of cysteine for a residue at position 84 and a substitution of serine for a residue at position 420 in the amino acid sequence of SEQ ID NO: 1;

(28) a substitution of isoleucine for a residue at position 17 and a substitution of threonine for a residue at position 161 in the amino acid sequence of SEQ ID NO: 1;

(29) a substitution of threonine for a residue at position 161 and a substitution of histidine for a residue at position 420 in the amino acid sequence of SEQ ID NO: 1; and

(30) a substitution of isoleucine for a residue at position 17 and a substitution of histidine for a residue at position 420 in the amino acid sequence of SEQ ID NO: 1.

7. The polypeptide according to claim 2, which has one or more amino acid substitutions selected from the group consisting of:

a substitution of an uncharged amino acid or a nonpolar amino acid for a residue at position 161 in the amino acid sequence of SEQ ID NO: 1;

a substitution of an amino acid other than proline, glycine, cysteine, and threonine for a residue at position 420 in the amino acid sequence of SEQ ID NO: 1;

a substitution of a nonpolar amino acid for a residue at position 17 in the amino acid sequence of SEQ ID NO: 1;

a substitution of an uncharged amino acid for a residue at position 84 in the amino acid sequence of SEQ ID NO: 1;

a substitution of a basic amino acid for a residue at position 171 in the amino acid sequence of SEQ ID NO: 1;

a substitution of an uncharged amino acid for a residue at position 176 in the amino acid sequence of SEQ ID NO: 1;

a substitution of a nonpolar amino acid for a residue at position 262 in the amino acid sequence of SEQ ID NO: 1;

a substitution of a nonpolar amino acid for a residue at position 302 in the amino acid sequence of SEQ ID NO: 1;

a substitution of an uncharged amino acid for a residue at position 421 in the amino acid sequence of SEQ ID NO: 1;

a substitution of a nonpolar amino acid for a residue at position 435 in the amino acid sequence of SEQ ID NO: 1;

a substitution of a basic amino acid for a residue at position 29 in the amino acid sequence of SEQ ID NO: 1;

a substitution of an uncharged amino acid for a residue at position 42 in the amino acid sequence of SEQ ID NO: 1;

a substitution of a nonpolar amino acid for a residue at position 116 in the amino acid sequence of SEQ ID NO: 1;

a substitution of a nonpolar amino acid for a residue at position 153 in the amino acid sequence of SEQ ID NO: 1;

a substitution of a nonpolar amino acid for a residue at position 190 in the amino acid sequence of SEQ ID NO: 1;

a substitution of an uncharged amino acid for a residue at position 284 in the amino acid sequence of SEQ ID NO: 1;

a substitution of a nonpolar amino acid for a residue at position 209 in the amino acid sequence of SEQ ID NO: 1;

a substitution of a nonpolar amino acid for a residue at position 235 in the amino acid sequence of SEQ ID NO: 1;

a substitution of a nonpolar amino acid for a residue at position 236 in the amino acid sequence of SEQ ID NO: 1;

a substitution of an uncharged amino acid for a residue at position 408 in the amino acid sequence of SEQ ID NO: 1;

a substitution of an uncharged amino acid for a residue at position 418 in the amino acid sequence of SEQ ID NO: 1;

a substitution of a nonpolar amino acid for a residue at position 434 in the amino acid sequence of SEQ ID NO: 1;

a substitution of a nonpolar amino acid for a residue at position 442 in the amino acid sequence of SEQ ID NO: 1;

a substitution of a basic amino acid for a residue at position 3 in the amino acid sequence of SEQ ID NO: 1;

a substitution of an uncharged amino acid for a residue at position 11 in the amino acid sequence of SEQ ID NO: 1; and a substitution of a basic amino acid for a residue at position 151 in the amino acid sequence of SEQ ID NO: 1.

8. The polypeptide according to claim 2, which has one or more amino acid substitutions selected from the group consisting of:

a substitution of threonine or valine for a residue at position 161 in the amino acid sequence of SEQ ID NO: 1;

a substitution of histidine, serine, alanine, aspartic acid, glutamic acid, arginine, glutamine, asparagine, lysine, valine, or tryptophan for a residue at position 420 in the amino acid sequence of SEQ ID NO: 1;

a substitution of isoleucine or leucine for a residue at position 17 in the amino acid sequence of SEQ ID NO: 1;

a substitution of cysteine for a residue at position 84 in the amino acid sequence of SEQ ID NO: 1;

a substitution of arginine for a residue at position 171 in the amino acid sequence of SEQ ID NO: 1;

a substitution of serine for a residue at position 176 in the amino acid sequence of SEQ ID NO: 1;

a substitution of valine for a residue at position 262 in the amino acid sequence of SEQ ID NO: 1;

a substitution of isoleucine for a residue at position 302 in the amino acid sequence of SEQ ID NO: 1;

a substitution of threonine for a residue at position 421 in the amino acid sequence of SEQ ID NO: 1;

a substitution of alanine for a residue at position 435 in the amino acid sequence of SEQ ID NO: 1;
a substitution of lysine for a residue at position 29 in the amino acid sequence of SEQ ID NO: 1;
a substitution of tyrosine for a residue at position 42 in the amino acid sequence of SEQ ID NO: 1;
a substitution of leucine for a residue at position 116 in the amino acid sequence of SEQ ID NO: 1;
a substitution of phenylalanine for a residue at position 153 in the amino acid sequence of SEQ ID NO: 1;
a substitution of tyrosine for a residue at position 190 in the amino acid sequence of SEQ ID NO: 1;
a substitution of isoleucine for a residue at position 284 in the amino acid sequence of SEQ ID NO: 1;
a substitution of alanine for a residue at position 209 in the amino acid sequence of SEQ ID NO: 1;
a substitution of valine for a residue at position 235 in the amino acid sequence of SEQ ID NO: 1;
a substitution of isoleucine for a residue at position 236 in the amino acid sequence of SEQ ID NO: 1;
a substitution of threonine for a residue at position 408 in the amino acid sequence of SEQ ID NO: 1;
a substitution of leucine for a residue at position 418 in the amino acid sequence of SEQ ID NO: 1;
a substitution of alanine for a residue at position 434 in the amino acid sequence of SEQ ID NO: 1;
a substitution of valine for a residue at position 442 in the amino acid sequence of SEQ ID NO: 1;
a substitution of arginine for a residue at position 3 in the amino acid sequence of SEQ ID NO: 1;
a substitution of glycine for a residue at position 11 in the amino acid sequence of SEQ ID NO: 1; and
a substitution of histidine for a residue at position 151 in the amino acid sequence of SEQ ID NO: 1.

9. An isolated DNA encoding the polypeptide according to claim 1.

10. A vector comprising the DNA according to claim 9.

11. A transformant obtained by transforming a host cell with the vector according to claim 10.

12. A method for producing an optically active amino compound, the method comprising allowing a ketone compound to react, in the presence of an amino group donor, with a polypeptide or the transformant according to claim 11, and/or a processed product therefrom,
wherein the polypeptide has the following properties (i) to (iii):
(i) having at least 85% sequence identity to the amino acid sequence of SEQ ID NO: 1, wherein one or more amino acids have been substituted, deleted or inserted in said sequence;
(ii) being capable of catalyzing a reaction of 7-methoxy-2-tetralone to produce (S)-7-methoxy-2-aminotetralin in the presence of an amino group donor; and
(iii) having greater enzymatic catalytic activity than that of an aminotransferase consisting of the amino acid sequence of SEQ ID NO: 1.

13. The method according to claim 12, wherein the ketone compound is an unsymmetrical ketone represented by the following formula (1):

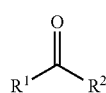

(1)

wherein $R^1$ and $R^2$ each represent an optionally substituted alkyl group, an optionally substituted aralkyl group, or an optionally substituted aryl group, and $R^1$ and $R^2$ may be linked together to form a ring, provided that $R^1$ and $R^2$ have different structures, and
a product of the reaction is an optically active amino compound represented by the following formula (2):

(2)

wherein $R^1$ and $R^2$ have the same meanings as in the formula (1), and * indicates an asymmetric carbon atom.

14. A method for producing an optically active amino compound, the method comprising allowing an enantiomeric mixture of amino compounds to react, in the presence of an amino group acceptor, with a polypeptide or the transformant according to claim 11, and/or a processed product therefrom,
wherein the polypeptide has the following properties (i) to (iii):
(i) having at least 85% sequence identity to the amino acid sequence of SEQ ID NO: 1;
(ii) being capable of catalyzing a reaction of 7-methoxy-2-tetralone to produce (S)-7-methoxy-2-aminotetralin in the presence of an amino group donor; and
(iii) having greater enzymatic catalytic activity than that of an aminotransferase consisting of the amino acid sequence of SEQ ID NO: 1.

15. The method according to claim 14, wherein the amino compounds form an enantiomeric mixture represented by the following formula (3):

(3)

wherein $R^1$ and $R^2$ each represent an optionally substituted alkyl group, an optionally substituted aralkyl group, or an optionally substituted aryl group, and $R^1$ and $R^2$ may be linked together to form a ring, provided that $R^1$ and $R^2$ have different structures, and
a product of the reaction is an optically active amino compound represented by the following formula (4):

(4)

wherein $R^1$ and $R^2$ have the same meanings as in the formula (3), and * indicates an asymmetric carbon atom.

16. The method according to claim 13, wherein the ketone compound represented by the formula (1) is at least one ketone compound selected from the group consisting of 1-tetralone, 2-tetralone, 5-methoxy-2-tetralone, 6-methoxy-2-tetralone, 7-methoxy-2-tetralone, 8-methoxy-2-tetralone, 1-benzyl-3-pyrrolidinone, 1-Boc-3-pyrrolidinone, 1-Cbz-3-pyrrolidinone, 1-benzyl-3-piperidinone, 1-Boc-3-piperidinone, 1-Cbz-3-piperidinone, acetophenone, and 3,4-dimethoxyphenylacetone.

17. The method according to claim 15, wherein the amino compound represented by the formula (3) is at least one amino compound selected from the group consisting of 1-aminotetralin, 2-aminotetralin, 5-methoxy-2-aminotetralin, 6-methoxy-2-aminotetralin, 7-methoxy-2-aminotetralin, 8-methoxy-2-aminotetralin, 1-benzyl-3-aminopyrrolidine, 1-Boc-3-aminopyrrolidine, 1-Cbz-3-aminopyrrolidine, 1-benzyl-3-aminopiperidine, 1-Boc-3-aminopiperidine, 1-Cbz-3-aminopiperidine, 1-phenethylamine, and 3,4-dimethoxyamphetamine.

18. The method according to claim 12, wherein the amino group donor is at least one compound selected from the group consisting of 1-phenethylamine, 2-butylamine, 2-pentylamine, 2-heptylamine, 3-heptylamine, n-ethylamine, n-propylamine, n-butylamine, n-amylamine, isopropylamine, isobutylamine, glycine, alanine, glutamic acid, 3-amino-1-phenylbutane, benzylamine, β-phenethylamine, cyclohexylamine, and optically active compounds thereof.

19. The method according to claim 14, wherein the amino group acceptor is pyruvic acid or glyoxylic acid.

20. The method according to claim 12, further comprising keeping the reaction at a temperature of at least 35° C.

* * * * *